US012805844B2

(12) United States Patent
Jeong et al.

(10) Patent No.: US 12,805,844 B2
(45) Date of Patent: Nov. 24, 2026

(54) ULTRASONIC DIAGNOSTIC APPARATUS AND CONTROL METHOD THEREOF

(71) Applicant: SAMSUNG MEDISON CO., LTD., Hongcheon-gun (KR)

(72) Inventors: Taegyun Jeong, Hongcheon-gun (KR); Yonghwan Kim, Hongcheon-gun (KR); Jusun Lee, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 19/053,549

(22) Filed: Feb. 14, 2025

(65) Prior Publication Data

US 2025/0331825 A1 Oct. 30, 2025

(30) Foreign Application Priority Data

Apr. 30, 2024 (KR) ........................ 10-2024-0057935
Oct. 24, 2024 (KR) ........................ 10-2024-0146315

(51) Int. Cl.
*A61B 8/00* (2006.01)
*A61B 8/08* (2006.01)
(Continued)

(52) U.S. Cl.
CPC .......... *A61B 8/5223* (2013.01); *A61B 8/0883* (2013.01); *A61B 8/0891* (2013.01); *A61B 8/463* (2013.01); *G06T 7/62* (2017.01); *G06T 7/66* (2017.01); *A61B 2576/023* (2013.01); *G06T 2207/10132* (2013.01);
(Continued)

(58) Field of Classification Search
CPC ... A61B 8/5223; A61B 8/0883; A61B 8/0891; A61B 8/463; A61B 2576/023; A61B 8/4444; A61B 8/461; A61B 8/5215; A61B 8/54; A61B 8/565; A61B 2503/40; G06T 7/62; G06T 7/66; G06T 2207/10132; G06T 2207/20081; G06T 2207/30048;
(Continued)

(56) References Cited

U.S. PATENT DOCUMENTS

2019/0019287 A1* 1/2019 Reda ...................... G06V 40/14
2019/0304098 A1 10/2019 Chen
(Continued)

FOREIGN PATENT DOCUMENTS

CN 113160254 A 7/2021
CN 115690047 A 2/2023
(Continued)

*Primary Examiner* — Kaitlyn E Sebastian
(74) *Attorney, Agent, or Firm* — Harvest IP Law, LLP

(57) ABSTRACT

Disclosed are an ultrasonic diagnostic apparatus and a control method thereof, the control method of an ultrasonic diagnostic apparatus including obtaining an animal ultrasonic image, extracting a cross-sectional image including cross sections of a plurality of target structures from the animal ultrasonic image, obtaining a processed image including contouring images of the plurality of target structures from the cross-sectional image, obtaining a center of gravity of each of the contouring images, and obtaining length information of the target structures based on intersection points between at least one line passing through centers of gravity of the contouring images and boundaries of the contouring images.

10 Claims, 17 Drawing Sheets

D23

(51) Int. Cl.
*G06T 7/00* (2017.01)
*G06T 7/60* (2017.01)
*G06T 7/62* (2017.01)
*G06T 7/66* (2017.01)

(52) U.S. Cl.
CPC ............... *G06T 2207/20081* (2013.01); *G06T 2207/30048* (2013.01); *G06T 2207/30101* (2013.01)

(58) Field of Classification Search
CPC . G06T 2207/30101; G06T 2207/20084; G06T 7/0012; G06T 7/60; G06T 2207/30004
See application file for complete search history.

(56) References Cited

U.S. PATENT DOCUMENTS

| | | | | |
|---|---|---|---|---|
| 2022/0280133 A1* | 9/2022 | McLeod | ................ | A61B 8/461 |
| 2023/0119535 A1 | 4/2023 | Michiels | | |
| 2023/0267605 A1 | 8/2023 | Liu | | |
| 2023/0267618 A1* | 8/2023 | Gogna | ................... | G16H 30/40<br>382/131 |

FOREIGN PATENT DOCUMENTS

| | | | |
|---|---|---|---|
| KR | 10-2018-0130511 | A | 12/2018 |
| KR | 10-2022-0032405 | A | 3/2022 |
| KR | 10-2022-0122540 | A | 9/2022 |

* cited by examiner

D21

ULTRASONIC DIAGNOSTIC APPARATUS AND CONTROL METHOD THEREOF

CROSS-REFERENCE TO RELATED APPLICATION(S)

This application is based on and claims priority under 35 U.S.C. § 119 to Korean Patent Application Nos. 10-2024-0057935 and 10-2024-0146315, filed on Apr. 30, 2024 and Oct. 24, 2024, in the Korean Intellectual Property Office, the disclosure of which is incorporated by reference herein in its entirety.

BACKGROUND

1. Field

The disclosure relates to an ultrasonic diagnostic apparatus for obtaining an ultrasonic image and a control method thereof.

2. Description of the Related Art

Recently, in a medical field, various medical imaging apparatuses have been widely used to image and obtain information about biological tissues of a human body for the purpose of early diagnosis of various diseases or surgery. Representative examples of such medical imaging apparatuses may include ultrasonic diagnostic apparatuses, Computed Tomography (CT) apparatuses, and Magnetic Resonance Imaging (MRI) apparatuses.

An ultrasonic imaging apparatus is a device that emits an ultrasonic signal generated from a transducer of a probe to an object, and non-invasively obtains at least one image of a region inside the object (e.g., soft tissue or blood flow) by receiving information from the signal reflected from the object. In particular, an ultrasonic diagnostic apparatus is used for medical purposes such as observing the inside of an object, detecting foreign substances, and measuring injury. Such an ultrasonic diagnostic apparatus is widely used together with other imaging diagnostic apparatuses because the ultrasonic imaging apparatus has higher stability than a diagnostic apparatus using an X-ray, may display images in real time, and is safe because there is no radiation exposure.

In animal echocardiography, a diameter ratio of a left atrium (LA) and an aorta (AO) is an important indicator for evaluating the health of a heart, especially whether the left atrium is enlarged, and therefore, accurate measurement of the diameter ratio of the left atrium and the aorta is required.

However, because each veterinarian defines boundaries of a heart structure based on different criteria, errors in measurement results between veterinarians may occur, which may lead to inaccurate diagnosis.

SUMMARY

It is an aspect of the disclosure to provide an ultrasonic diagnostic apparatus and a control method thereof, which aims to determine a boundary between a left atrium and an aorta using a machine learning model in an animal heart ultrasonic image, and measure a diameter ratio of the left atrium and the aorta according to a standardized criterion.

Additional aspects of the disclosure will be set forth in part in the description which follows and, in part, will be obvious from the description, or may be learned by practice of the disclosure.

In accordance with an aspect of the disclosure, a control method of an ultrasonic diagnostic apparatus may include obtaining an animal ultrasonic image, extracting a cross-sectional image including cross sections of a plurality of target structures from the animal ultrasonic image, obtaining a processed image including contouring images of the plurality of target structures from the cross-sectional image, obtaining a center of gravity of each of the contouring images, and obtaining length information of the target structures based on intersection points between at least one line passing through centers of gravity of the contouring images and boundaries of the contouring images.

In accordance with an aspect of the disclosure, an ultrasonic diagnostic apparatus may include a probe configured to transmit an ultrasonic signal to an object and receive an echo signal reflected from the object, a display configured to display an ultrasonic image obtained based on echo information received by the probe, an input interface configured to receive user input, and a processor configured to control the probe to obtain an animal ultrasonic image, extract a cross-sectional image including cross sections of a plurality of target structures from the animal ultrasonic image, obtain a processed image including contouring images of the plurality of target structures from the cross-sectional image, obtain a center of gravity of each of the contouring images, and obtain length information of the target structures based on intersection points between at least one line passing through centers of gravity of the contouring images and boundaries of the contouring images.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
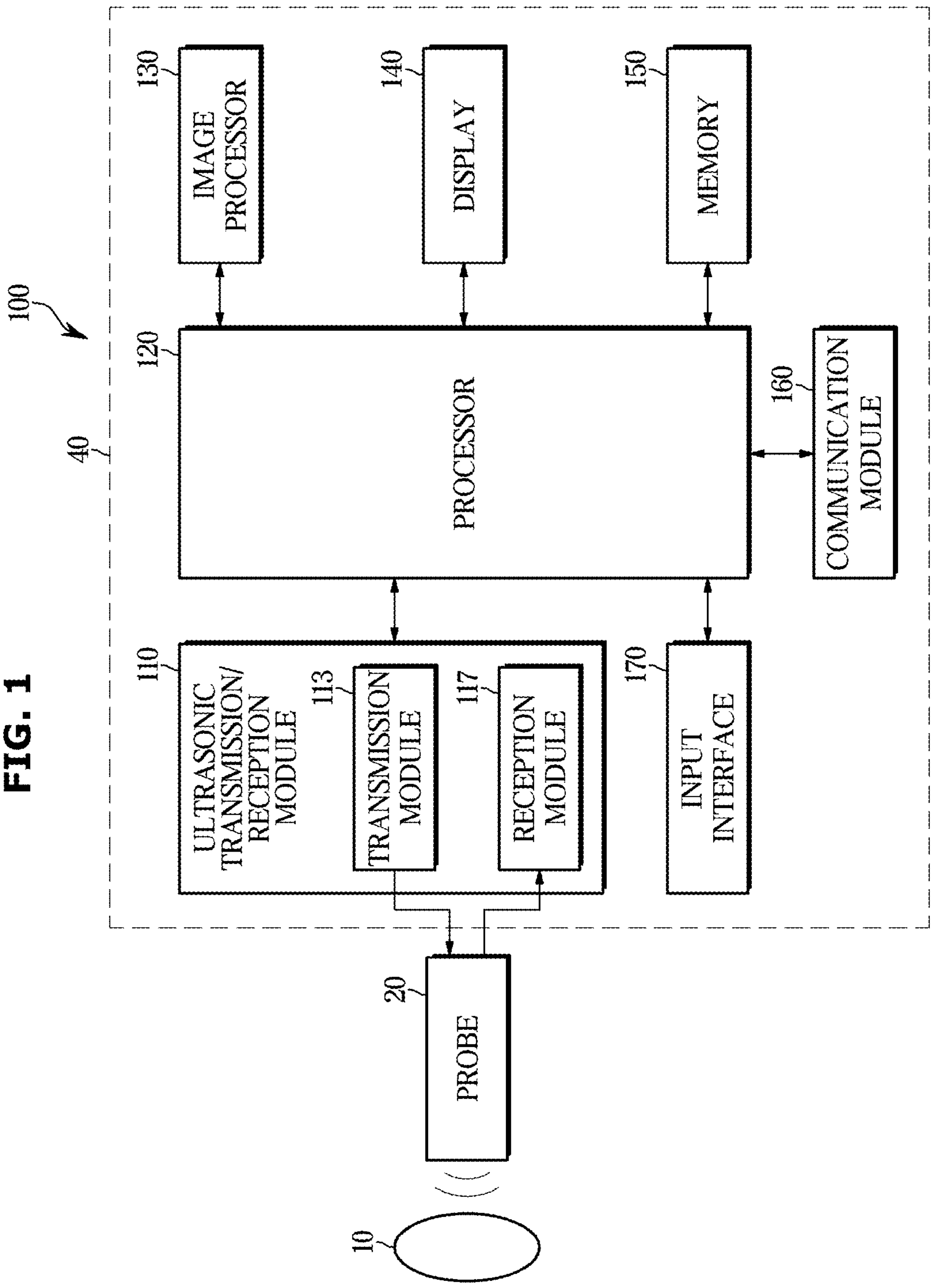
FIG. 1 illustrates a control block diagram of an ultrasonic imaging system in a case in which a probe is a wired probe or a hybrid probe.

This disclosure will explain the principles and disclose embodiments of the disclosure to clarify the scope of the claims of the disclosure and enable those skilled in the art to which the embodiments of the disclosure belong to practice the embodiments. The embodiments of the disclosure may be implemented in various forms.

Throughout the specification, like reference numbers refer to like elements. This specification does not describe all components of the embodiments, and general contents in the technical field to which the disclosure belongs or overlapping contents between the embodiments will not be described. The "module" or "unit" used in the specification may be implemented as one or a combination of two or more of software, hardware, and firmware, and according to embodiments, a plurality of "module" or "unit" may be implemented as a single element, or a single "module" or "unit" may include a plurality of elements.

The singular form of a noun corresponding to an item may include a single item or a plurality of items, unless the relevant context clearly indicates otherwise.

In this disclosure, each of phrases such as "A or B," "at least one of A and B," "at least one of A or B," "A, B or C," "at least one of A, B and C," and "at least one of A, B, or C" may include any one of the items listed together in the corresponding one of the phrases, or all possible combinations thereof.

The term "and/or" includes any combination of a plurality of related components or any one of a plurality of related components.

The terms such as "first," "second," "primary," and "secondary" may simply be used to distinguish a given component from other corresponding components, and do not limit the corresponding components in any other respect (e.g., importance or order).

The terms "front surface," "rear surface," "upper surface," "lower surface," "side surface," "left side," "right side," "upper portion," "lower portion," and the like used in the disclosure are defined with reference to the drawings, and the shape and position of each component are not limited by these terms.

The terms "comprises," "has," and the like are intended to indicate that there are features, numbers, steps, operations, components, parts, or combinations thereof described in the disclosure, and do not exclude the presence or addition of one or more other features, numbers, steps, operations, components, parts, or combinations thereof.

When any component is referred to as being "connected," "coupled," "supported," or "in contact" with another component, this includes a case in which the components are indirectly connected, coupled, supported, or in contact with each other through a third component as well as directly connected, coupled, supported, or in contact with each other.

When any component is referred to as being located "on" or "over" another component, this includes not only a case in which any component is in contact with another component but also a case in which another component is present between the two components.

Hereinafter, an ultrasonic device according to various embodiments will be described in detail with reference to the accompanying drawings. When described with reference to the attached drawings, similar reference numbers may be assigned to identical or corresponding components and redundant description thereof may be omitted.

In this disclosure, images may include a medical image obtained by a medical imaging apparatus, such as a magnetic resonance imaging (MRI) apparatus, a computed tomography (CT) apparatus, an ultrasonic imaging apparatus, and an x-ray imaging apparatus.

In this disclosure, an 'object', which is subject to photography, may include a person, animal, or part thereof. For example, the object may include a part of a human body (an organ, etc.) or a phantom.

Throughout this disclosure, an 'ultrasonic image' refers to an image of an object that has been processed based on an ultrasonic signal transmitted to and reflected from the object.

Hereinafter, embodiments will be described in detail with reference to the drawings.

Figure 2:
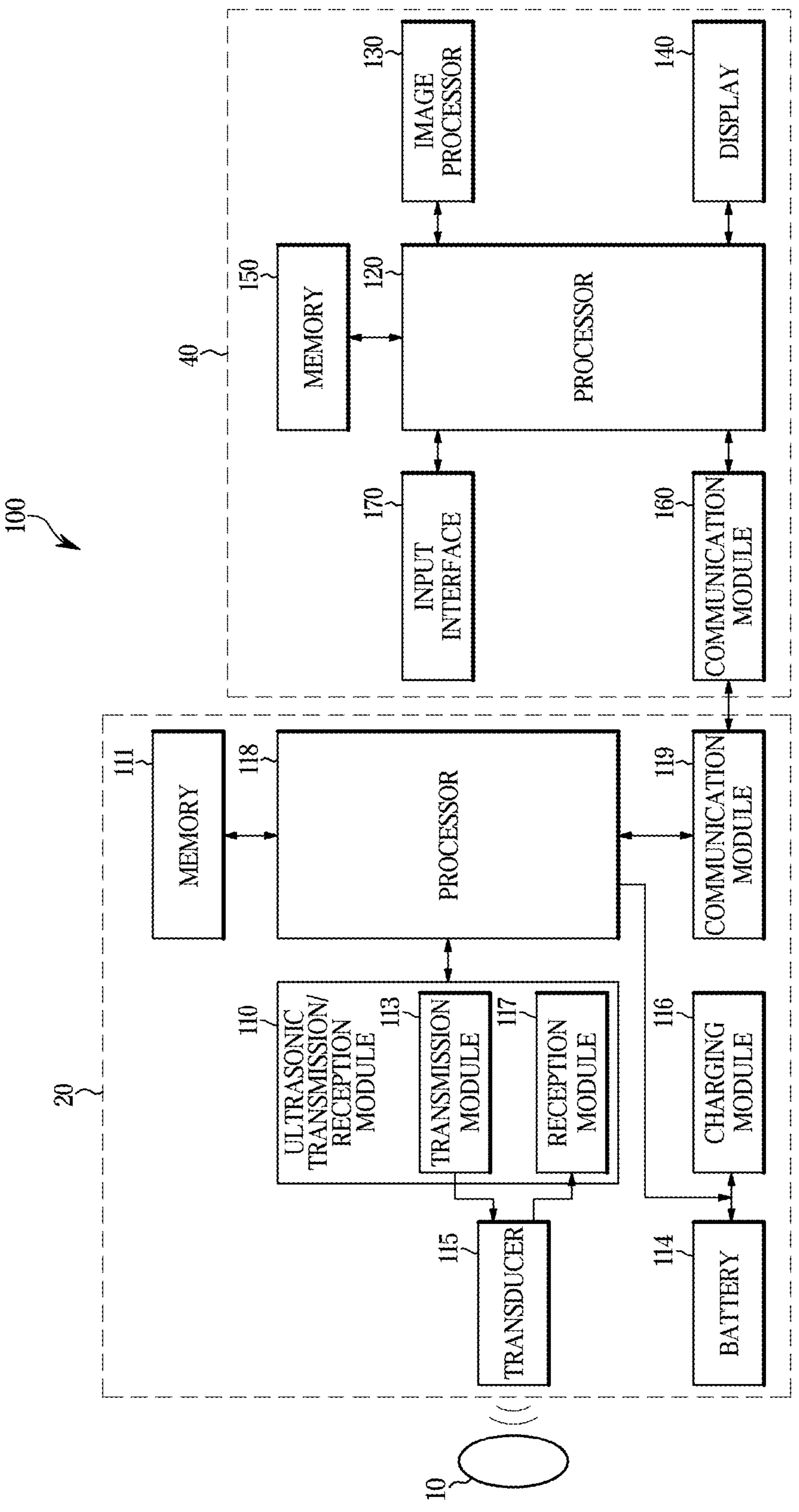
FIG. 2 illustrates a control block diagram of the ultrasonic imaging system in a case in which the probe is a wireless probe or a hybrid probe.

Referring to FIGS. 1 and 2, an ultrasonic imaging system 100 may include a probe 20 and an ultrasonic diagnostic apparatus 40.

The ultrasonic diagnostic apparatus 40 may be implemented not only in a cart type but also in a portable type. A portable ultrasonic imaging apparatus may include, for example, a smart phone, laptop computer, Personal Digital Assistant (PDA), tablet Personal Computer (PC), etc., which include a probe and an application, but is not limited thereto.

The probe 20 may include a wired probe connected to the ultrasonic diagnostic apparatus 40 by wire to communicate with the ultrasonic diagnostic apparatus 40 by wire, a wireless probe wirelessly connected to the ultrasonic diagnostic apparatus 40 to communicate wirelessly with the ultrasonic diagnostic apparatus 40, and/or a hybrid probe by wire or wirelessly connected to the ultrasonic diagnostic apparatus 40 to communicate by wire or wirelessly with the ultrasonic diagnostic apparatus 40.

According to various embodiments, as illustrated in FIG. 1, the ultrasonic diagnostic apparatus 40 may include an ultrasonic transmission/reception module 110, or as illustrated in FIG. 2, the probe 20 may include the ultrasonic transmission/reception module 110. According to various embodiments, both the ultrasonic diagnostic apparatus 40 and the probe 20 may also include the ultrasonic transmission/reception module 110.

According to various embodiments, the ultrasonic diagnostic apparatus 40 may further include an image processor 130, a display 140, and/or an input interface 170. In addition, the image processor 130, the display 140, and/or the input interface 170 may also be included in the probe 20. Accordingly, the descriptions of the ultrasonic transmission/reception module 110, the image processor 130, the display 140, and/or the input interface 170 included in the ultrasonic diagnostic apparatus 40 may also be applied to the ultrasonic transmission/reception module 110, the image processor 130, the display 140, and/or the input interface 170 included in the probe 20.

FIG. 1 illustrates a control block diagram of the ultrasonic imaging system 100 in a case in which the probe 20 is a wired probe or a hybrid probe.

The probe 20 may include a plurality of transducers. The plurality of transducers may transmit an ultrasonic signal to an object 10 in response to a transmission signal applied from a transmission module 113. The plurality of transducers may form a received signal by receiving the ultrasonic signal (echo signal) reflected from the object 10. The probe

20 may be implemented as an integrated type with the ultrasonic diagnostic apparatus 40, or may be implemented as a separate type connected to the ultrasonic diagnostic apparatus 40 by wire. The ultrasonic diagnostic apparatus 40 may be connected to the one or more probes 20 depending on the implementation type.

In a case in which the probe 20 is a wired probe or a hybrid probe, the probe 20 may include a cable and a connector capable of being connected to a connector of the ultrasonic diagnostic apparatus 40.

The probe 20 according to an embodiment may be implemented as a two-dimensional probe. In a case in which the probe 20 is implemented as a two-dimensional probe, the plurality of transducers included in the probe 20 may be arranged in two dimensions to form a two-dimensional transducer array.

For example, the two-dimensional transducer array may have a form in which a plurality of sub-arrays including the plurality of transducers arranged in a first direction is arranged in a second direction different from the first direction.

In addition, in the case in which the probe 20 according to an embodiment is implemented as a two-dimensional probe, the ultrasonic transmission/reception module 110 may include an analog beamformer and a digital beamformer. Alternatively, the two-dimensional probe may include one or both of the analog beamformer and the digital beamformer depending on the implementation type.

A processor 120 controls the transmission module 113 to form a transmission signal to be applied to each of the transducers 115 in consideration of positions and focused points of the plurality of transducers included in the probe 20.

The processor 120 may control a reception module 117 to generate ultrasonic data by converting reception signals received from the probe 20 to analog to digital and summing up the digitally converted reception signals in consideration of the positions and focused points of the plurality of transducers.

In the case in which the probe 20 is implemented as a two-dimensional probe, the processor 120 may calculate a time delay value for digital beamforming for each sub-array for each of the plurality of sub-arrays included in the two-dimensional transducer array. The processor 120 may also calculate a time delay value for analog beamforming for each of the transducers included in one of the plurality of sub-arrays. The processor 120 may control the analog beamformer and the digital beamformer to form a transmission signal to be applied to each of the plurality of transducers depending on the time delay values for analog beamforming and the time delay values for digital beamforming. The processor 120 may also control the analog beamformer to sum up the signals received from the plurality of transducers for each sub-array depending on the time delay values for analog beamforming. The processor 120 may also control the ultrasonic transmission/reception module 110 to convert the summed signal for each sub-array from analog to digital. The processor 120 may also control the digital beamformer to generate ultrasonic data by summing up the digitally converted signals depending on the time delay values for digital beamforming.

The image processor 130 generates an ultrasonic image using the generated ultrasonic data.

The display 140 may display the generated ultrasonic image and a variety of information processed by the ultrasonic diagnostic apparatus 40 and/or the probe 20. The probe 20 and/or the ultrasonic diagnostic apparatus 40 may include the one or more displays 140 depending on the implementation type. The display 140 may also include a touch panel or a touch screen.

The display 140 may output four-dimensional ultrasonic images according to control commands of the processor 120. The four-dimensional ultrasonic image may mean providing three-dimensional images in real time by adding the dimension of time. For example, the four-dimensional ultrasonic image may be an ultrasonic image that includes fetal movements, heartbeats, or other motions of a biological tissue over time. The four-dimensional ultrasonic image may be implemented based on ultrasonic image data obtained in real time or ultrasonic image data previously stored in memory 150.

The processor 120 may control the overall operation of the ultrasonic diagnostic apparatus 40 and signal flows between internal components of the ultrasonic diagnostic apparatus 40. The processor 120 may perform or control various operations or functions of the ultrasonic diagnostic apparatus 40 by executing programs or instructions stored in the memory 150. The processor 120 may also control an operation of the ultrasonic diagnostic apparatus 40 by receiving a control signal from the input interface 170 or an external device.

The ultrasonic diagnostic apparatus 40 may include a communication module 160, and may be connected to an external device (e.g., the probe 20, a server, medical device, portable device (a smart phone, tablet PC, wearable device, etc.)) through the communication module 160.

The communication module 160 may include one or more components that enable communication with the external device, and may include, for example, at least one of a short-range communication module, a wired communication module, and a wireless communication module.

The communication module 160 may receive a control signal and data from the external device, and may transmit the received control signal to the processor 120 to enable the processor 120 to control the ultrasonic diagnostic apparatus 40 in response to the received control signal.

Alternatively, the processor 120 may transmit a control signal to the external device through the communication module 160 to control the external device in response to the control signal of the processor.

For example, the external device may process data in the external device in response to the control signal of the processor received through the communication module.

A program capable of controlling the ultrasonic diagnostic apparatus 40 may be installed in the external device, and this program may include instructions for performing some or all of the operations of the processor 120.

The program may be pre-installed on the external device, or a user of the external device may download and install the program from a server providing an application. The server providing the application may include a recording medium in which the program is stored.

The memory 150 may store various data or programs for driving and controlling the ultrasonic diagnostic apparatus 40, inputted and outputted ultrasonic data, ultrasonic images, etc.

The input interface 170 may receive user input for controlling the ultrasonic diagnostic apparatus 40. For example, the user input may include, but is not limited to, input of manipulating a button, a keypad, a mouse, a trackball, a jog switch, a knob, and the like, input of touching a touch pad or touch screen, voice input, motion input, biometric information input (e.g., iris recognition, fingerprint recognition, etc.), and the like.

FIG. 2 illustrates a control block diagram of the ultrasonic imaging system 100 in a case in which the probe 20 is a wireless probe or a hybrid probe.

According to various embodiments, the ultrasonic diagnostic apparatus 40 illustrated in FIG. 2 may be replaced with the ultrasonic diagnostic apparatus 40 described with reference to FIG. 1.

According to various embodiments, the probe 20 illustrated in FIG. 1 may be replaced with the probe 20 to be described with reference to FIG. 2.

The probe 20 may include the transmission module 113, a battery 114, the transducer 115, a charging module 116, the reception module 117, a processor 118, and a communication module 119. Although FIG. 1 illustrates that the probe 20 includes both the transmission module 113 and the reception module 117, the probe 20 may include only part of a configuration of the transmission module 113 and the reception module 117 depending on the implementation type, and the part of the configuration of the transmission module 113 and the reception module 117 may be included in the ultrasonic diagnostic apparatus 40. Alternatively, the probe 20 may further include the image processor 130.

The transducer 115 may include a plurality of transducers. The plurality of transducers may transmit an ultrasonic signal to the object 10 in response to a transmission signal applied from the transmission module 113. The plurality of transducers may receive the ultrasonic signal reflected from the object 10 to form a reception signal.

The charging module 116 may charge the battery 114. The charging module 116 may receive electric power from the outside. The charging module 116 may receive electric power wirelessly. However, the disclosure is not limited thereto, and the charging module 116 may receive electric power by wire. The charging module 116 may transfer the received electric power to the battery 114.

The processor 118 controls the transmission module 113 to form a transmission signal to be applied to each of the plurality of transducers in consideration of the positions and focused points of the plurality of transducers.

The processor 118 controls the reception module 117 to generate ultrasonic data by converting reception signals received from the transducer 115 from analog to digital and summing up the digitally converted reception signals in consideration of the positions and focused points of the plurality of transducers. Alternatively, in a case in which the probe 20 includes the image processor 130, the probe 20 may generate an ultrasonic image using the generated ultrasonic data.

In the case in which the probe 20 is implemented as a two-dimensional probe, the processor 118 may calculate a time delay value for digital beamforming for each sub-array for each of the plurality of sub-arrays included in the two-dimensional transducer array. The processor 118 may also calculate a time delay value for analog beamforming for each of the transducers included in one of the plurality of sub-arrays. The processor 118 may control the analog beamformer and the digital beamformer to form a transmission signal to be applied to each of the plurality of transducers depending on the time delay values for analog beamforming and the time delay values for digital beamforming. The processor 118 may also control the analog beamformer to sum up the signals received from the plurality of transducers for each sub-array depending on the time delay values for analog beamforming. The processor 118 may also control the ultrasonic transmission/reception module 110 to convert the summed signal for each sub-array from analog to digital. The processor 118 may also control the digital beamformer to generate ultrasonic data by summing up the digitally converted signals depending on the time delay values for digital beamforming.

The processor 118 may control the overall operation of the probe 20 and the signal flows between the internal components of the probe 20. The processor 118 may perform or control the various operations or functions of the probe 20 by executing programs or instructions stored in memory 111. The processor 118 may also control the operation of the probe 20 by receiving a control signal from the input interface 170 of the probe 20 or an external device (e.g., the ultrasonic diagnostic apparatus 40).

The communication module 119 may wirelessly transmit the generated ultrasonic data or ultrasonic images to the ultrasonic diagnostic apparatus 40 through a wireless network. The communication module 119 may also receive a control signal and data from the ultrasonic diagnostic apparatus 40.

The ultrasonic diagnostic apparatus 40 may receive the ultrasonic data or ultrasonic images from the probe 20.

In an embodiment, in the case in which the probe 20 includes the image processor 130 capable of generating ultrasonic images using the ultrasonic data, the probe 20 may transmit the ultrasonic data and/or the ultrasonic images generated by the image processor 130 to the ultrasonic diagnostic apparatus 40.

In an embodiment, in a case in which the probe 20 does not include the image processor 130 capable of generating ultrasonic images using the ultrasonic data, the probe 20 may transmit the ultrasonic data to the ultrasonic diagnostic apparatus 40. The ultrasonic data may include ultrasonic raw data, and the ultrasonic images may refer to ultrasonic image data.

The ultrasonic diagnostic apparatus 40 may include the processor 120, the image processor 130, the display 140, the memory 150, the communication module 160, and the input interface 170.

The image processor 130 generates ultrasonic images using the ultrasonic data received from the probe 20.

The display 140 may display the ultrasonic images received from the probe 20, ultrasonic images generated by processing the ultrasonic data received from the probe 20, and a variety of information processed by the ultrasonic imaging system 100. The ultrasonic diagnostic apparatus 40 may include the one or more displays 140 depending on the implementation type. The display 140 may also include a touch panel or a touch screen.

The processor 120 may control the overall operation of the ultrasonic diagnostic apparatus 40 and the signal flows between the internal components of the ultrasonic diagnostic apparatus 40. The processor 120 may perform or control the various operations or functions of the ultrasonic diagnostic apparatus 40 by executing the programs or applications stored in the memory 150. The processor 120 may also control the operation of the ultrasonic diagnostic apparatus 40 by receiving a control signal from the input interface 170 or an external device.

The ultrasonic diagnostic apparatus 40 may include the communication module 160, and may be connected to an external device (e.g., the probe 20, a server, medical device, portable device (a smart phone, tablet PC, wearable device, etc.)) through the communication module 160.

The communication module 160 may include one or more components that enable communication with the external device, and may include, for example, at least one of the short-range communication module, the wired communication module, and the wireless communication module.

The communication module 160 of the ultrasonic diagnostic apparatus 40 and the communication module 119 of the probe 20 may communicate using a network or a short-range wireless communication method. For example, the communication module 160 of the ultrasonic diagnostic apparatus 40 and the communication module 119 of the probe 20 may communicate using any one of wireless Local Area Network (LAN), Wi-Fi, Bluetooth, ZigBee, Wi-Fi Direct (WFD), Infrared Data Association (IrDA), Bluetooth Low Energy (BLE), Near Field Communication (NFC), Wireless Broadband Internet (WiBro), World Interoperability for Microwave Access (WiMAX), Shared Wireless Access Protocol (SWAP), Wireless Gigabit Alliance (WiGig), Radio Frequency (RF) communication, a wireless data communication method including 60 GHz millimeter wave (mm wave) short-range communication, etc.

To this end, the communication module 160 of the ultrasonic diagnostic apparatus 40 and the communication module 119 of the probe 20 may include at least one of a wireless LAN communication module, a Wi-Fi communication module, a Bluetooth communication module, a ZigBee communication module, a Wi-Fi Direct (WFD) communication module, an Infrared Data Association (IrDA) communication module, a Bluetooth Low Energy (BLE) communication module, a Near Field Communication (NFC) module, a Wireless Broadband Internet (WiBro) communication module, a World Interoperability for Microwave Access (WiMAX) communication module, a Shared Wireless Access Protocol (SWAP) communication module, a Wireless Gigabit Alliance (WiGig) communication module, a RF communication module, and a 60 GHz millimeter wave (mm wave) short-range communication module.

In an embodiment, the probe 20 may transmit device information (e.g., ID information) of the probe 20 using a first communication method (e.g., BLE), may be wirelessly paired with the ultrasonic diagnostic apparatus 40, and may transmit ultrasonic data and/or ultrasonic images to the paired ultrasonic diagnostic apparatus 40.

The device information of the probe 20 may include a variety of information related to a serial number, model name, and battery state of the probe 20.

The ultrasonic diagnostic apparatus 40 may receive the device information (e.g., ID information) of the probe 20 from the probe 20 using the first communication method (e.g., BLE), may be wirelessly paired with the probe 20, may transmit an activation signal to the paired probe 20, and may receive the ultrasonic data and/or ultrasonic images from the probe 20. In this case, the activation signal may include a signal for controlling the operation of the probe 20.

In an embodiment, the probe 20 may transmit the device information (e.g., ID information) of the probe 20 using the first communication method (e.g., BLE), may be wirelessly paired with the ultrasonic diagnostic device 40, and may transmit the ultrasonic data and/or ultrasonic images to the ultrasonic diagnostic apparatus 40 paired by the first communication method using a second communication method (e.g., 60 GHz millimeter wave and Wi-Fi).

The ultrasonic diagnostic apparatus 40 may receive the device information (e.g., ID information) of the probe 20 from the probe 20 using the first communication method (e.g., BLE), may be wirelessly paired with the probe 20, may transmit the activation signal to the paired probe 20, and may receive the ultrasonic data and/or ultrasonic images from the probe 20 using the second communication method (e.g., 60 GHz millimeter wave and Wi-Fi).

According to various embodiments, the first communication method used to pair the probe 20 and the ultrasonic diagnostic apparatus 40 with each other may have a lower frequency band than a frequency band of the second communication method used by the probe 20 to transmit the ultrasonic data and/or ultrasonic images to the ultrasonic diagnostic apparatus 40.

The display 140 of the ultrasonic diagnostic apparatus 40 may display User Interfaces (UIs) indicating the device information of the probe 20. For example, the display 140 may display UIs, which indicate identification information of the wireless probe 20, a pairing method indicating how to pair with the probe 20, a data communication state between the probe 20 and the ultrasonic diagnostic apparatus 40, a method of performing data communication with the ultrasonic diagnostic apparatus 40, and the battery state of the probe 20.

In a case in which the probe 20 includes the display 140, the display 140 of the probe 20 may display UIs indicating the device information of the probe 20. For example, the display 140 may display UIs, which indicate the identification information of the wireless probe 20, the pairing method indicating how to pair with the probe 20, the data communication state between the probe 20 and the ultrasonic diagnostic apparatus 40, the method of performing data communication with the ultrasonic diagnostic apparatus 40, and the battery state of the probe 20.

The communication module 160 may also receive a control signal and data from an external device and transmit the received control signal to the processor 120 so that the processor 120 controls the ultrasonic diagnostic apparatus 40 in response to the received control signal.

Alternatively, the processor 120 may transmit a control signal to an external device through the communication module 160 to control the external device in response to the control signal of the processor 120.

For example, the external device may process data of the external device in response to the control signal of the processor 120 received through the communication module.

A program capable of controlling the ultrasonic diagnostic apparatus 40 may be installed in the external device, and this program may include instructions for performing some or all of the operations of the processor 120.

The program may be pre-installed on the external device, or a user of the external device may download and install the program from a server providing the application. The server providing the application may include the recording medium in which the program is stored.

The memory 150 may store various data or programs for driving and controlling the ultrasonic diagnostic apparatus 40, inputted and outputted ultrasonic data, ultrasonic images, etc.

Examples of the ultrasonic imaging system 100 according to an embodiment of the disclosure will be described later through FIGS. 3, 4, 5, and 6.

FIGS. 3, 4, 5, and 6 are views illustrating ultrasonic imaging apparatuses according to an embodiment.

Figure 3:
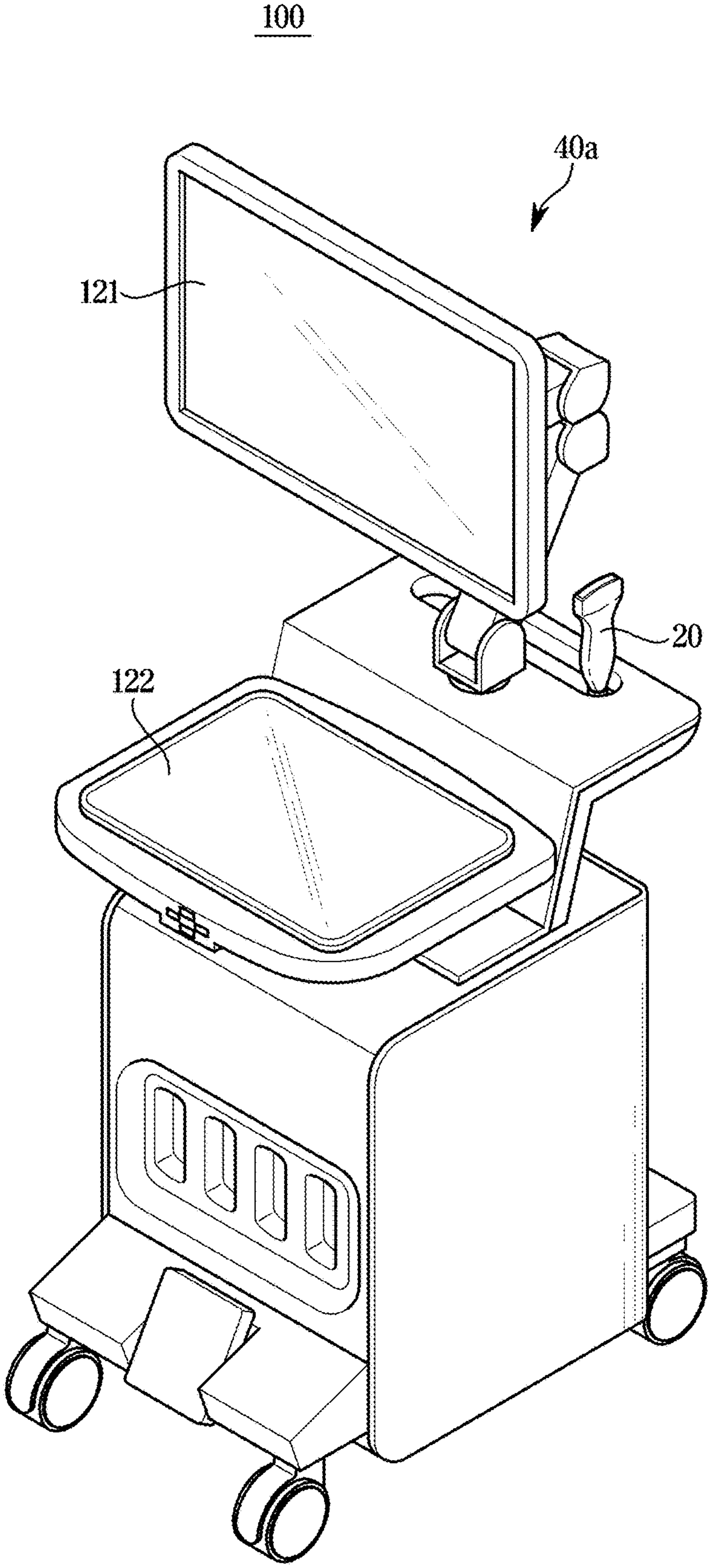
FIGS. 3 to 6 are views illustrating the ultrasonic imaging system according to an embodiment.
Figure 4:
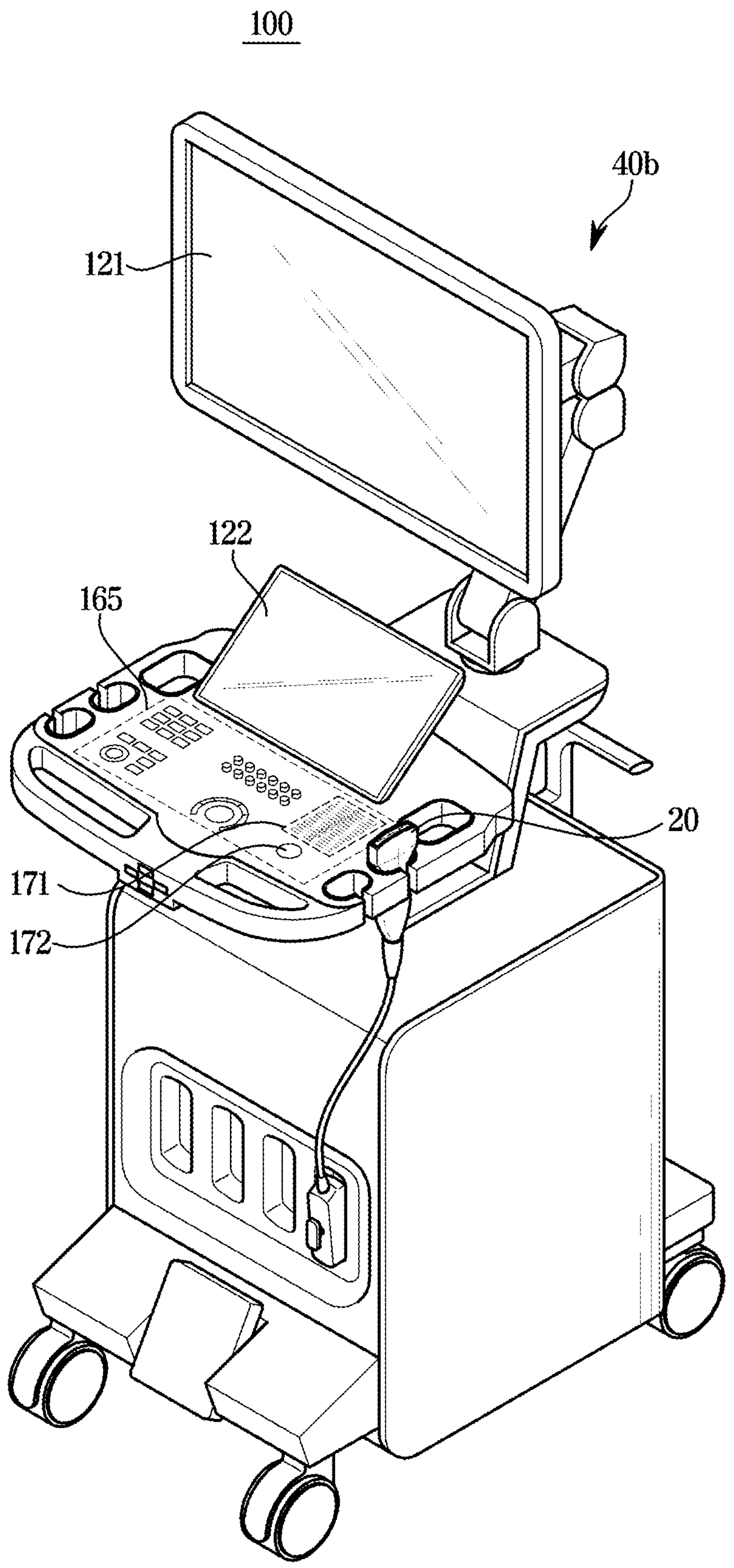

Referring to FIGS. 3 and 4, ultrasonic imaging apparatuses 40*a* and 40*b* may include a main display 121 (140) and a sub display 122 (140). At least one of the main display 121 and the sub display 122 may be implemented as a touch screen. At least one of the main display 121 and the sub display 122 may display ultrasonic images or a variety of information processed by the ultrasonic imaging apparatuses 40*a* and 40*b*. In addition, at least one of the main display 121 and the sub display 122 may be implemented as a touch screen and provide Graphical User Interfaces (GUIs), so that data for controlling the ultrasonic imaging apparatuses 40*a* and 40*b* may be inputted from a user. For example, the main display 121 may display ultrasonic images, and the sub display 122 may display a control panel (e.g., control panel 165 in FIG. 4) for controlling the display of the ultrasonic images in the form of GUIs. The sub display 122 may be provided with data for controlling the display of images through the control panel displayed in the form of GUIs. For example, a time gain compensation (TGC) button, a Freeze button, a trackball, a jog switch, a knob, and the like may be provided as GUIs on the sub display 122.

The ultrasonic imaging apparatuses 40*a* and 40*b* may control the display of ultrasonic images displayed on the main display 121 using the inputted control data. The ultrasonic imaging apparatuses 40*a* and 40*b* may also be connected to the probe 20 by wire or wirelessly to transmit and receive ultrasonic signals to and from the object.

Referring to FIG. 4, the ultrasonic imaging apparatus 40*b* may further include a control panel 165 in addition to the main display 121 and the sub display 122. The control panel 165 may include a button, a trackball, a jog switch, a knob, and the like, and may be provided with data for controlling the ultrasonic imaging apparatus 40*b* from the user. For example, the control panel 165 may include a time gain compensation (TGC) button 171, a Freeze button 172, and the like. The TGC button 171 is a button for setting a TGC value for each depth of the ultrasonic images. When the input of the Freeze button 172 is sensed while scanning an ultrasonic image, the ultrasonic imaging apparatus 40*b* may maintain a state in which the frame image at that point in time is displayed.

A button, a trackball, a jog switch, a knob, and the like included in the control panel 165 may be provided as GUIs on the main display 121 or the sub display 122. The ultrasonic imaging apparatuses 40*a* and 40*b* may be connected to the probe 20 to transmit and receive ultrasonic signals to and from the object.

Figure 5:
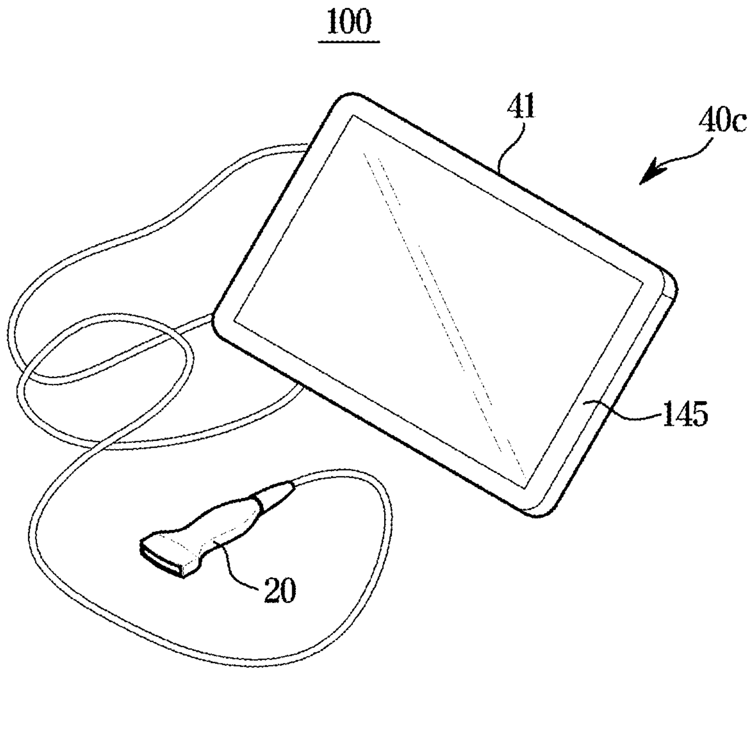
Figure 6:
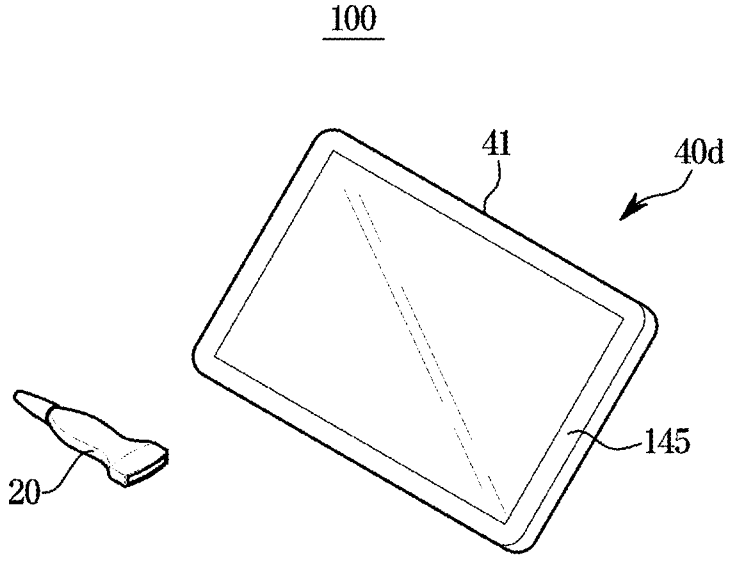

Referring to FIGS. 5 and 6, ultrasonic diagnostic apparatuses 40*c* and 40*d* may be implemented in a portable type. The portable ultrasonic imaging apparatuses 40*c* and 40*d* may include, for example, a smart phone, laptop computer, PDA, tablet PC, etc., which include a probe and an application, but is not limited thereto.

The ultrasonic imaging apparatus 40*c* may include a main body 41. Referring to FIG. 5, the probe 20 may be connected to one side of the main body 41 by wire. To this end, the main body 41 may include a connection terminal to and from which a cable connected to the probe 20 may be attached and detached, and the probe 20 may include a connection terminal to and from which a cable connected to the main body 41 may be attached and detached.

Referring to FIG. 6, the probe 20 may be wirelessly connected to the ultrasonic diagnostic apparatus 40*d*. The main body 41 may include an input/output interface (e.g., a touch screen) 145 (the display 140 and the input interface 170). Ultrasonic images, a variety of information processed by the ultrasonic imaging apparatus, GUIs, and the like may be displayed on the input/output interface 145.

An ultrasonic image may be displayed on the input/output interface 145. The ultrasonic imaging apparatuses 40*c* and 40*d* may correct the ultrasonic image displayed on the input/output interface 145 using artificial intelligence (AI). The ultrasonic imaging apparatus 40*c* may provide an alarm for informing using various audio-visual tools, such as graphics, sound, and vibration, information about lesions among the ultrasonic images displayed on the input/output interface 145 using AI.

The ultrasonic imaging apparatuses 40*c* and 40*d* may output a control panel displayed in the form of GUIs through the input/output interface 145.

An ultrasonic imaging apparatus 40*d* and the probe 20 may establish communication or be paired using a short-range wireless communication. For example, the ultrasonic imaging apparatus 40*d* and the probe 20 may perform communication using Bluetooth, BLE, Wi-Fi, or Wi-Fi Direct.

The ultrasonic imaging apparatuses 40*c* and 40*d* may execute a program or application related to the probe 20 to control the probe 20 and output information related to the probe 20. The ultrasonic imaging apparatuses 40*c* and 40*d* may perform operations related to the probe 20 while communicating with a predetermined server. The probe 20 may be registered with the ultrasonic imaging apparatuses 40*c* and 40*d* or may be registered with the predetermined server. The ultrasonic imaging apparatuses 40*c* and 40*d* may communicate with the registered probe 20 and perform the operations related to the probe 20.

The ultrasonic imaging apparatuses 40*c* and 40*d* may include various types of input/output interfaces such as speakers, Light Emitting Diodes (LEDs), and vibration devices. For example, the ultrasonic imaging apparatuses 40*c* and 40*d* may output a variety of information in the form of graphics, sound, or vibration through the input/output interface. The ultrasonic imaging apparatuses 40*c* and 40*d* may also output various notifications or data through the input/output interface.

According to an embodiment of the disclosure, the ultrasonic imaging apparatus 40*a*, 40*b*, 40*c*, or 40*d* may process ultrasonic images or obtain additional information from ultrasonic images, using an artificial intelligence (AI) model. According to an embodiment of the disclosure, the ultrasonic imaging apparatus 40*a*, 40*b*, 40*c*, or 40*d* may generate an ultrasonic image or perform processing such as correction, image quality improvement, encoding, and decoding on the ultrasonic image, using an AI model. In addition, according to an embodiment of the disclosure, the ultrasonic imaging apparatus 40*a*, 40*b*, 40*c*, or 40*d* may perform processing, such as baseline definition, anatomical information acquisition, lesion information acquisition, surface extraction, boundary definition, length measurement, area measurement, volume measurement, and annotation creation, on ultrasonic images using the AI model.

The AI model may be provided on the ultrasonic imaging apparatus 40*a*, 40*b*, 40*c*, or 40*d*, or may be provided on a server.

The AI model may be implemented using various artificial neural network models or deep neural network models. In addition, the AI model may be learned (trained) and created using various machine learning algorithms or deep learning algorithms. The AI model may be implemented using, for example, a model such as a convolutional neural network (CNN), a recurrent neural network (RNN), a generative adversarial network (GAN), and a long short-term memory (LSTM) network.

Figure 7:
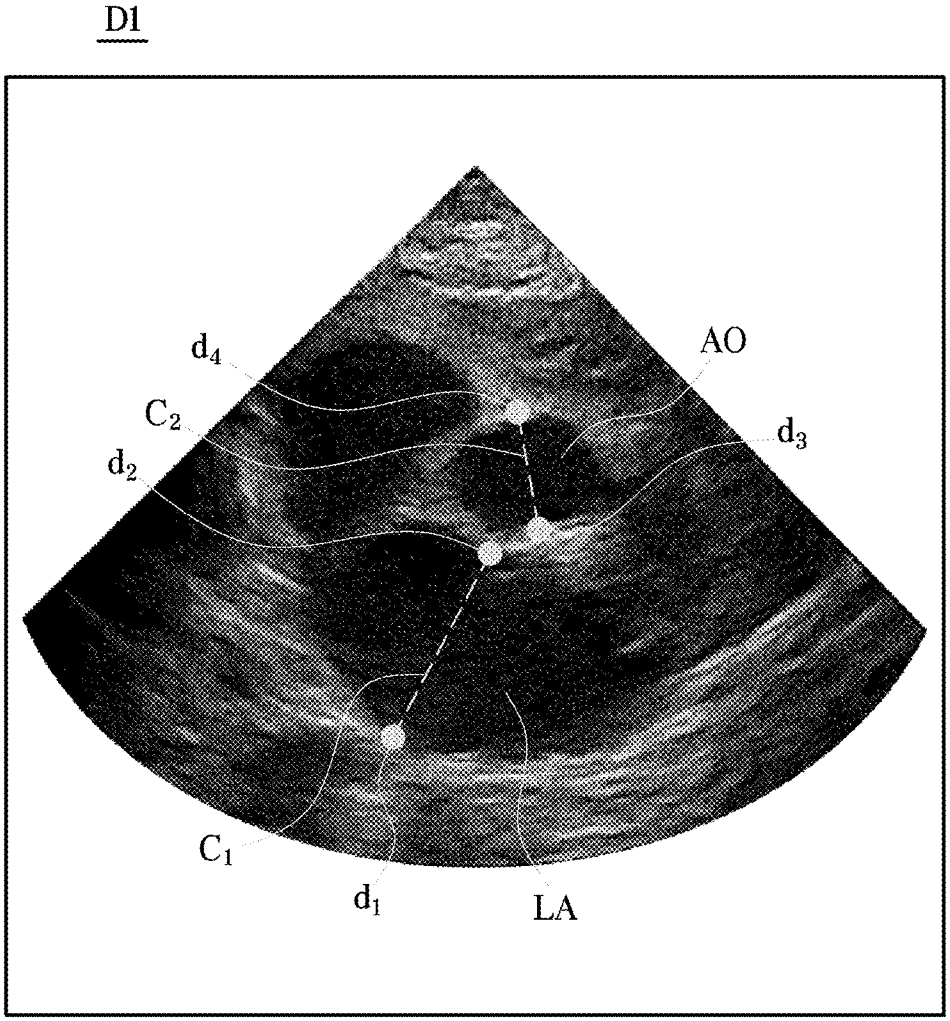
FIG. 7 illustrates an example of an animal echocardiographic cross-sectional image and a method of manually measuring a diameter ratio of a left atrium and an aorta in an embodiment.

FIG. 7 illustrates a method of manually measuring a diameter ratio of a left atrium and an aorta in an embodiment.

According to various embodiments, the user may specify two points on an ultrasonic cross-sectional image and measure a distance between the two points, using buttons, a keypad, a mouse, a trackball, or the like of the input interface 170. For example, the user may obtain length information (e.g., length, area, or width) of structures included in an animal echocardiography cross-sectional image using the Caliper function.

Specifically, the user may mark on the animal echocardiography cross-sectional image (e.g., D1 in FIG. 7). In other words, the user may place a marker on the animal echocardiography cross-sectional image using buttons, a keypad, a mouse, a trackball, or the like of the input interface 170. In this case, the marking may involve selecting and marking specific points on the animal echocardiography cross-sectional image. When the user inputs a command regarding marking through the input interface 170, the processor 120, which has received the command, may display at least one indicator (for example, $d_1$, $d_2$, $d_3$, or $d_4$ in FIG. 7) related to the marking at a specific point on the animal echocardiography cross-sectional image based on the command of the user.

Accordingly, the processor 120 may measure a distance between two points specified by the user. For example, when the user specifies two points $d_1$ and $d_2$ to measure a diameter of a left atrium LA, the processor 120 may measure a distance between the two points $d_1$ and $d_2$. In addition, when the user specifies two points $d_3$ and $d_4$ to measure a diameter of an aorta AO, the processor 120 may measure a distance between the two points $d_3$ and $d_4$. Accordingly, the processor 120 may measure a diameter ratio of the left atrium and the aorta. In this case, the processor 120 may display on the animal echocardiography cross-sectional image a line connecting two points (e.g., $C_1$ and $C_2$ in FIG. 7) that serve as references for measuring each diameter, together with at least one indicator (e.g., $d_1$, $d_2$, $d_3$, or $d_4$ in FIG. 7) associated with a specific point marking.

However, when the length information of structures included in the cross-sectional image is measured manually using the cross-sectional image, because positions of the two points that serve as the basis for length measurement are determined based on experience or subjective judgment of the user, errors may occur even when identical structures included in the same cross-sectional image are measured.

Figure 8:
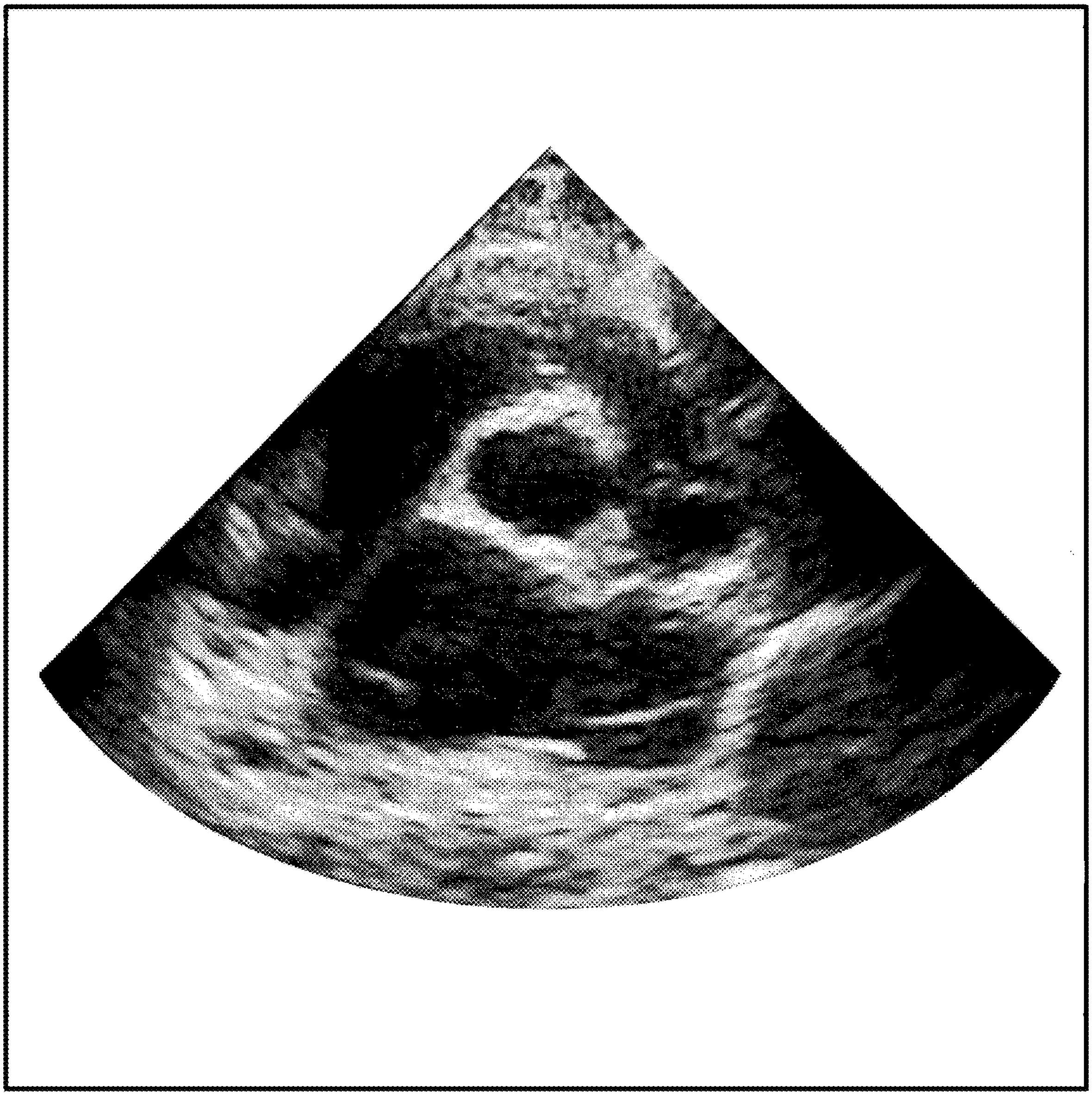
FIG. 8 illustrates an example of input data input to a machine learning model according to an embodiment.

FIG. 8 illustrates an example of input data input to a machine learning model according to an embodiment.

According to an embodiment, the processor 120 may obtain an animal ultrasonic image and extract a cross-sectional image included in the animal ultrasonic image.

The cross-sectional image may be obtained from one of image frames included in the obtained ultrasonic image. In this case, the ultrasonic image may be a real-time ultrasonic image obtained from an echo signal received by the probe 20 as an ultrasonic signal emitted from the probe 20 to the object is reflected and returned as an echo signal. Also, the ultrasonic image may be an ultrasonic image stored in memory 150.

According to an embodiment, the ultrasonic image obtained by the processor 120 may include a parasternal short axis (PSAX) view image obtained by placing the probe 20 next to a sternum of an animal and emitting ultrasonic waves in a transverse direction of a heart. Accordingly, the cross-sectional image obtained from the ultrasonic image may include a cross-sectional image (e.g., D21 in FIG. 8) obtained based on a short-axis of the animal heart.

The cross-sectional image obtained from the parasternal short axis (PSAX) view image shows a cross-section of the heart and allows observation of several heart structures at once. Therefore, because several important heart structures, such as a left ventricle, the aorta and left atrium, may be identified, the cross-sectional image may be usefully used to evaluate the condition of heart valves or heart muscles.

In addition, the cross-sectional image may also be useful in observing contraction and relaxation states of the heart and blood flow.

The user may measure the length, area, or width of the left atrium or aorta included in the cross-sectional image using the cross-sectional image obtained from the parasternal short axis (PSAX) view image.

Additionally, the user may measure the diameter ratio of the left atrium and the aorta using the cross-sectional image obtained from the parasternal short axis (PSAX) view image in diagnosing heart function and heart valve abnormalities.

Figure 9:
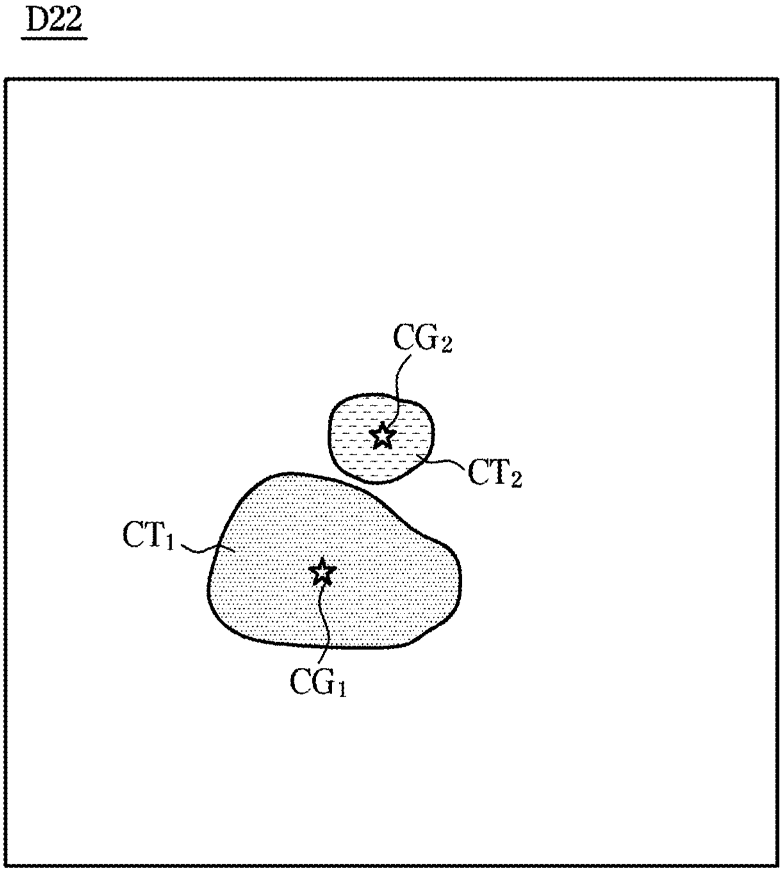
FIG. 9 illustrates an example of output data output from the machine learning model according to an embodiment.

FIG. 9 illustrates an example of output data output from the machine learning model according to an embodiment.

According to an embodiment, the processor 120 may input a cross-sectional image as input data into the AI model and obtain a processed image including contouring images of a plurality of target structures included in the cross-sectional image as output data.

In this case, the target structure may include a structure that is an object of measurement for obtaining the length information. For example, in obtaining information on a diameter of the left atrium, the target structure may be a cross section of the left atrium. Also, in obtaining information on a diameter of the aorta, the target structure may be a cross section of the aorta. As another example, in obtaining information on the diameter ratio of the left atrium and the aorta, the target structures may be the cross section of the left atrium and the cross section of the aorta. The target structure may be determined based on the user input received from the input interface 170. For example, the user may directly set a target structure (e.g., an organ, lesion, tumor, etc.) through the input interface 170. In addition, the processor 120 may determine a preset target structure as the target structure based on a mode or application selected by the user through the input interface 170.

The contouring image is an image for tracking a boundary of a target structure (e.g., an organ, lesion, tumor, etc.) and visually conveying information about the boundary of the target structure.

For example, referring to FIG. 9, the processed image may include a contouring image $CT_1$ of a left atrium cross-section and a contouring image $CT_2$ of an aorta cross-section based on what is determined to be the left atrial cross-section and the aortic cross-section as the target structures. Although the processed image of FIG. 9 only shows contouring images without any indication of the cross-sectional image, which is the input data, the processed image may be implemented in a form in which the contouring images overlap the cross-sectional image, which is the input data.

According to an embodiment, the processor 120 may display a variety of information about the target structures along with contouring images of the target structures on the processed image obtained from a machine learning model.

For example, as illustrated in FIG. 9, the processor 120 may also calculate a center of gravity of each contouring image and display indicators (e.g., $CG_1$ and $CG_2$ in FIG. 9) indicating the center of gravity. In this case, a known image processing method may be used as a method in which the processor 120 calculates the center of gravity of each contouring image. As an example, the processor 120 may binarize contouring images and calculate coordinate values of all pixels belonging to the binarized contouring images by a taking weighted average. That is, the processor 120 may calculate the center of gravity by adding up the product of coordinates of each pixel and a pixel value for each of x and y axes and dividing this by the total number of pixels of a structure.

Hereinafter, a method of obtaining processed data using the machine learning model using the cross-sectional image obtained by the processor 120 as input data will be described in detail with reference to FIG. 10.

Figure 10:
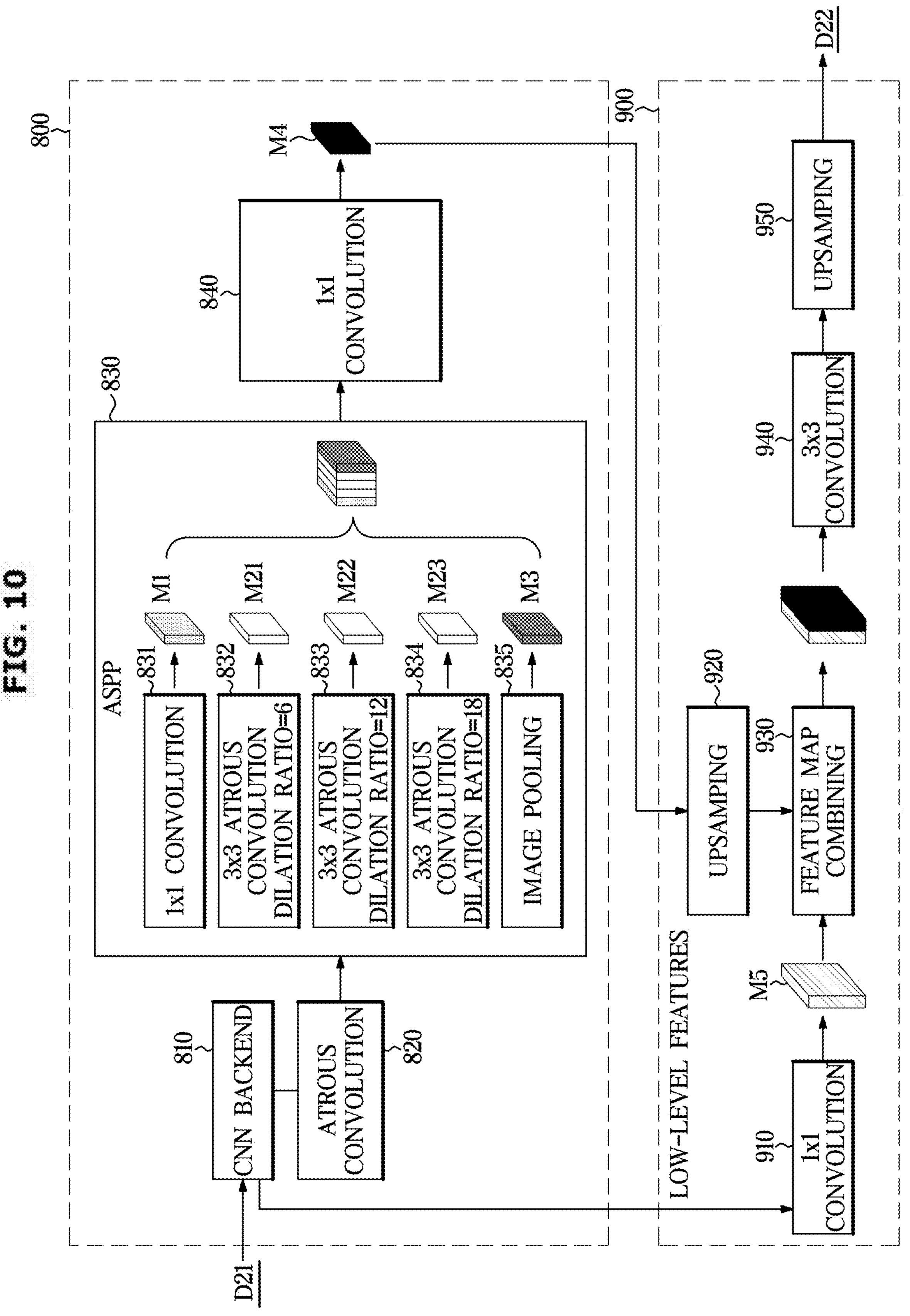
FIG. 10 is a diagram for explaining a method of obtaining a processed image including contouring images of a plurality of target structures using the machine learning model according to an embodiment.

FIG. 10 is a diagram for explaining a method of obtaining a processed image including contouring images of a plurality of target structures using the AI model according to an embodiment.

The AI model according to an embodiment may include an encoder 800 and a decoder 900.

According to an embodiment, the processor 120 may input the input data (e.g., D21) to the encoder 800 to extract features of a cross-sectional image. In other words, when the processor 120 inputs the input data to the encoder 800, one feature map M4 including features extracted from the cross-sectional image input as input data may be created. In other words, the processor 120 may perform a segmentation task using the AI model using the cross-sectional image obtained from the ultrasonic image as input data.

The encoder 800 may include CNN backend 810, atrous convolution 820, atrous spatial pyramid pooling (ASPP) 830, and 1×1 convolution 840.

The CNN backend 810 may perform multiple layers of convolution operations to transform the input image into abstract features. That is, low-level features may be extracted from an initial layer of the CNN backend 810, and the low-level features may contain a lot of detailed boundary or texture information of the input image. Therefore, the low-level features may be used to restore important details in the decoder 900.

The atrous convolution 820 is similar to a basic convolution, but a receptive area passing through each filter may be expanded by leaving an interval between the filters of a kernel. Accordingly, through this, information may be obtained from a large area without reducing the resolution of an image. The atrous convolution 820 may be included in the CNN backend 810. In other words, the atrous convolution 820 may be used in a specific layer of the CNN backend 810.

For example, while general convolution extracts features from a small area, the atrous convolution 820 may effectively process context information in a large area by increasing the interval between pixels. Accordingly, an important object boundary and context information may be simultaneously obtained in an image segmentation task.

The ASPP 830 may train the object boundary and context information using atrous convolution filters of different sizes. The ASPP 830 may obtain information at various scales of an image through various sized filters and various expansion ratios. For example, the ASPP 830 may include 1×1 convolution 831, 3×3 atrous convolution 832 with a 6 dilation ratio, 3×3 atrous convolution 833 with a 12 dilation ratio, and 3×3 atrous convolution 834 with an 18 dilation ratio. The ASPP 830 may extract detailed features from a small area using a small filter, and extract abstract and broad features from a large area using a large filter.

The ASPP 830 may also add global context information of the entire image through image pooling 835 operation.

The ASPP 830 may create a combined feature map by combining these multi-scale feature maps M1, M21, M22, M23, and M3.

The 1×1 convolution 840 may reduce complex information, in which feature maps of multiple channels are combined, into a single channel. Accordingly, the 1×1 convolution 840 may increase computational efficiency and create a more concise representation before transferring the complex information to a multi-scale information decoder.

The 1×1 convolution 840 may condense and summarize information obtained from multiple scales by combining all feature map channels at each location. The feature map M4 created in this way may be delivered to the decoder 900, and detailed segmentation may be performed.

The decoder 900 may perform detailed image segmentation by converting a low-resolution feature map extracted from the encoder 800 into a high-resolution map.

The decoder 900 may combine the low-level features extracted from the initial layer of the encoder 800 back into the high-level feature map M4. Because the low-level features contain detailed information such as boundaries or texture information of the cross-sectional image input as input data, the boundaries of segmentation may be restored more accurately by combining the low-level features.

However, because the low-level features also contain a lot of unnecessary information, the decoder 900 may refine the information or remove unimportant channels through 1×1 convolution 910 operation. Accordingly, the decoder 900 may extract a low-level feature map M5 in a refined form.

The decoder 900 may perform upsampling 920 and 950, which gradually enlarges the low-resolution feature map M4. Accordingly, a processed image of the same size as the cross-sectional image input as input data may be generated as output data.

For example, the decoder 900 may convert the low-resolution features to medium resolution by enlarging the feature map M4 through the first upsampling 920.

In this process, the decoder 900 may create a combined feature map (930 operation) by combining the low-level features, the low-level feature map M5 in a refined form obtained through the 1×1 convolution 910 operation, and a mid-resolution feature map on which the first upsampling has been performed.

Thereafter, the decoder 900 may supplement detailed information of the image through 3×3 convolution 940 operation.

The decoder 900 may obtain a processed image (e.g., D22) having the same resolution as the cross-sectional image input as input data through the second upsampling 950.

That is, the decoder 900 may generate a high-resolution processed image that matches a cross-sectional image size input as input data based on the low-level features and high-level features extracted from the encoder 800.

Figure 11:
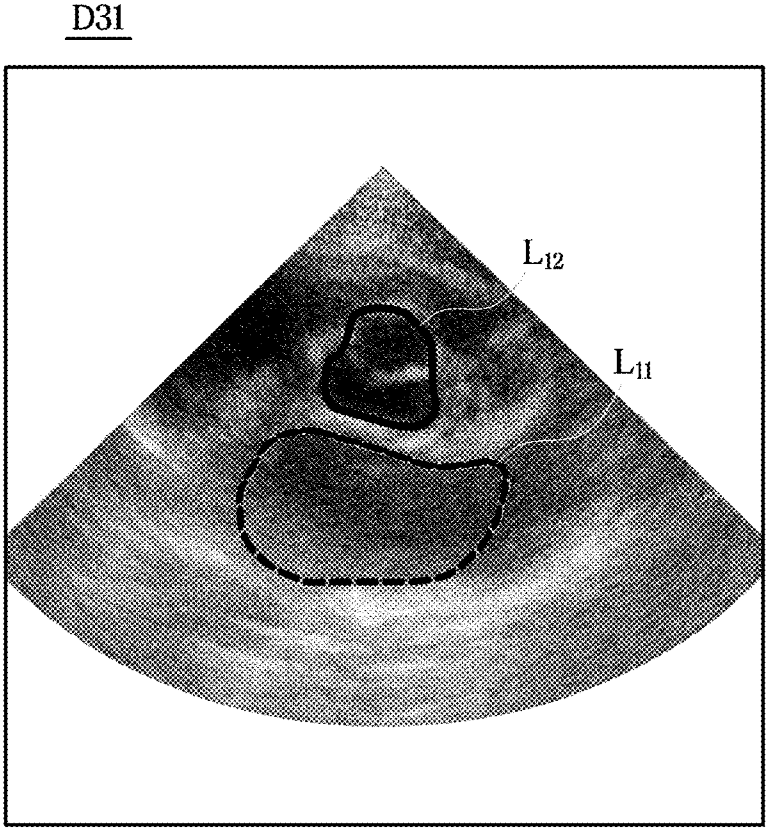
FIG. 11 illustrates an example of training data for training the machine learning model.

FIG. 11 illustrates an example of training data for training the machine learning model.

Figure 12:
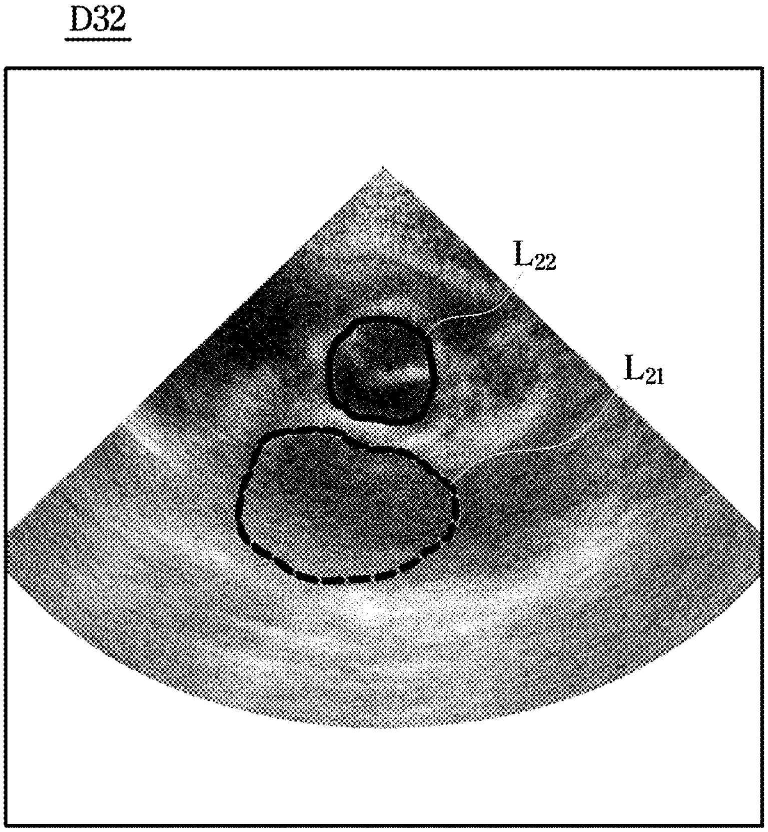
FIG. 12 illustrates another example of training data for training the machine learning model.

FIG. 12 illustrates another example of training data for training the machine learning model.

According to an embodiment, the processor 120 may train the AI model through supervised learning. In other words, the processor 120 may train the AI model to generate desired output data using input data and correct answer data corresponding thereto. In this case, the correct answer data may be referred to as labeling data.

In this case, the processor 120 may prepare the input data and the correct answer data, measure a loss function, which is a difference between the output data of the AI model and the correct answer data, in a process in which the AI model training, and repeat a process of adjusting parameters of the AI model based on the measured loss function multiple times (epochs). Accordingly, an error between the output data of the AI model and the correct answer data may be reduced, and accurate output data may be output. In this process, the processor 120 may evaluate how well the AI model has been learned using test data. In this case, the generalization ability of the AI model may be checked by using data that is not input during the training of the AI model (i.e., 3rd party data) as test data.

In the training of the AI model, the correct answer data is very important to improve the generalization ability of the AI model. The correct answer data is data that serves as the basis for training of the AI model, and accurate and diverse correct answer data must be secured so that the AI model may output accurate output data in various situations.

In particular, in performing the segmentation task, input data must be accurately labeled in a correct class (e.g., person, background). When the correct answer data is incomplete or contains incorrect labels, the AI model may not be able to learn pixel by pixel.

In this case, the labeling of the input data may include marking the boundary of a structure to obtain a contouring image of the structure in the cross-sectional image.

For example, the labeling of the input data may include marking boundaries of the left atrial cross-section and the aortic cross-section by a veterinarian to obtain contouring images of the left atrium cross-section and the aorta cross-section determined as target structures in the cross-sectional image.

In an embodiment, a cross-sectional image (e.g., D21 in FIG. 8) obtained from an ultrasonic image may be used as input data for training the AI model. In this case, the cross-sectional image may include target structures.

Referring to FIG. 11, as correct answer data for training the AI model, images $L_{11}$ and $L_{12}$ on which the boundary of each target structure capable of being checked in the cross-sectional image is marked may be included in the cross-sectional image D31. That is, data in which the veterinarian marks the boundary by reflecting a portion capable of being checked in the cross-sectional image as much as possible may be used as training data.

Additionally, referring to FIG. 12, in training the AI model, images $L_{21}$ and $L_{22}$ indicating boundaries of the respective target structures in which characteristic factors of the target structures are reflected may be additionally included in the cross-sectional image D32 as correct answer data. That is, data in which the veterinarian marks the boundary by considering even a portion capable of not being checked in the cross-sectional image in consideration of an original form of the target structure may be additionally used as training data.

According to an embodiment, in training the AI model, more generalized output data may be obtained from the AI model by using correct answer data labeled with two criteria as correct answer data.

Figure 13:
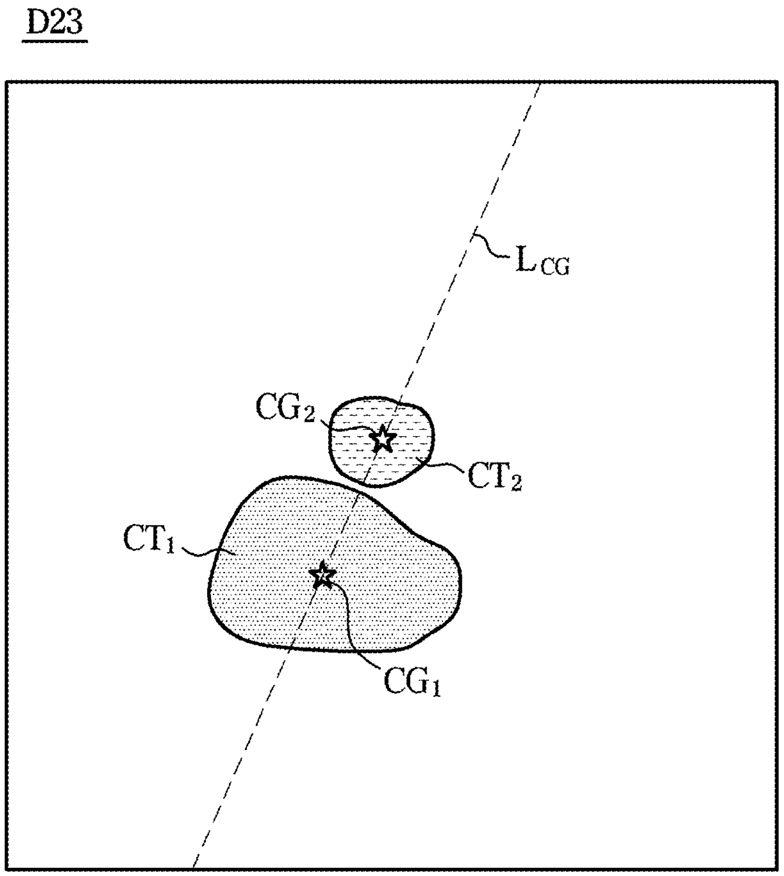
FIGS. 13 and 14 are diagrams for explaining an example of a standardized method of obtaining length information of the plurality of target structures from the processed image.
Figure 14:
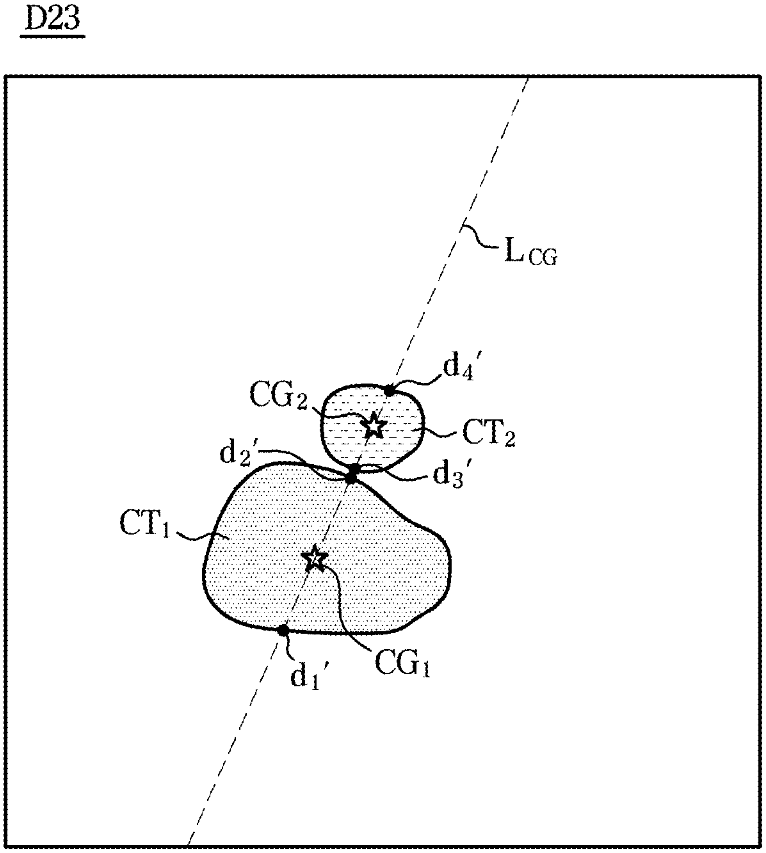

FIGS. 13 and 14 are diagrams for explaining an example of a standardized method of obtaining length information of the plurality of target structures from the processed image.

According to an embodiment, the processor 120 may obtain length information of target structures based on intersection points between at least one line passing through centers of gravity of contouring images and boundaries of the contouring images.

In this case, the obtaining of the length information of the target structures may include obtaining a diameter, width, area of each of the target structures or diameter ratios of the target structures.

For example, the obtaining of the length information of the target structures may include obtaining the diameters of the left atrium and the aorta or the diameter ratio of the left atrium and the aorta.

According to an embodiment, the processor 120 may also obtain length information of the target structure based on a line passing through all centers of gravity of the contouring images.

Referring to FIGS. 13 and 14, the processor 120 may calculate the diameter of the left atrium, the diameter of the aorta, or the diameter ratio of the left atrium and the aorta based on intersection points $d_{1'}$, $d_{2'}$, $d_{3'}$, and $d_{4'}$ between one line LCG passing through centers of gravities $CG_1$ and $CG_2$ of the respective contouring images of the left atrium and the aorta and the boundaries of the contouring images in the cross-sectional image D23.

Specifically, in calculating the diameter of the left atrium, the processor 120 may calculate a distance between $d_{1'}$ and $d_{2'}$, using $d_{1'}$ and $d_{2'}$, which are intersection points between the one line LCG passing through both the centers of gravity $CG_1$ and $CG_2$ and the boundary of the left atrium contouring image, as reference points. In calculating the diameter of the aorta, the processor 120 may also calculate a distance between $d_{3'}$ and $d_{4'}$, using $d_{3'}$ and $d_{4'}$, which are intersection points between the one line LCG passing through both the centers of gravity $CG_1$ and $CG_2$ and the boundary of the aorta contouring image, as reference points. Thereafter, the processor 120 may calculate a ratio of the distance between d1' and d2' and the distance between d3' and d4' in calculating the diameter ratio of the left atrium and the aorta.

According to an embodiment, factors causing inter-veterinarian and inter measurement-attempt errors may be eliminated by extracting length information of target structures based on a standardized method of connecting lines of centers of gravity of contouring images and boundaries of contouring images.

Figure 15:
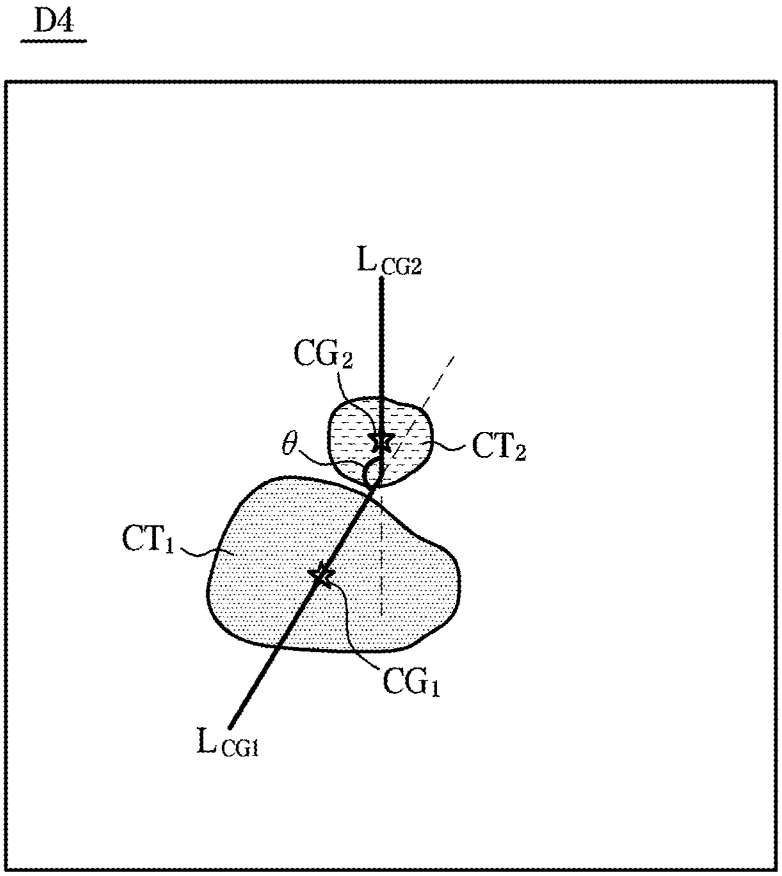
FIG. 15 is a diagram for explaining another example of a standardized method of obtaining the length information of the plurality of target structures from the processed image.

FIG. 15 is a diagram for explaining another example of a standardized method of obtaining the length information of the plurality of target structures from the processed image.

According to an embodiment, the processor 120 may obtain length information of target structures through a plurality of lines passing through respective centers of gravity of the contouring images, rather than through a line passing through all centers of gravity of the contouring images.

Referring to FIG. 15, the processor 120 can draw a first line $L_{CG1}$ passing through a center of gravity of the contouring image $CT_1$ of a first target structure on the cross-sectional image D4, and draw a second line $L_{CG2}$ passing through a center of gravity of the contouring image $CT_2$ of a second target to have a preset angle Θ with the first line $L_{CG1}$.

Accordingly, the processor 120 may obtain length information of the first target structure based on intersection points between the first line $L_{CG1}$ and a boundary of the contouring image $CT_1$ of the first target structure. The processor 120 may also obtain length information of the second target structure based on intersection points between the second line $L_{CG2}$ and a boundary of the contouring image $CT_2$ of the second target structure.

The processor 120 may determine the preset angle Θ between the first line $L_{CG1}$ and the second line $L_{CG2}$ based on the user input received through the input interface 170. For example, the processor 120 may receive in advance a size of the preset angle Θ through the input interface 170. As another example, the processor 120 may determine the size of the preset angle based on preset data stored in the memory 150 when receiving input related to the mode or application from the user through the input interface 170.

According to an embodiment, by drawing a plurality of lines passing through centers of gravity to obtain length information of target structures, appropriate length information may be obtained depending on a characteristic or diagnostic condition of each structure.

Figure 16:
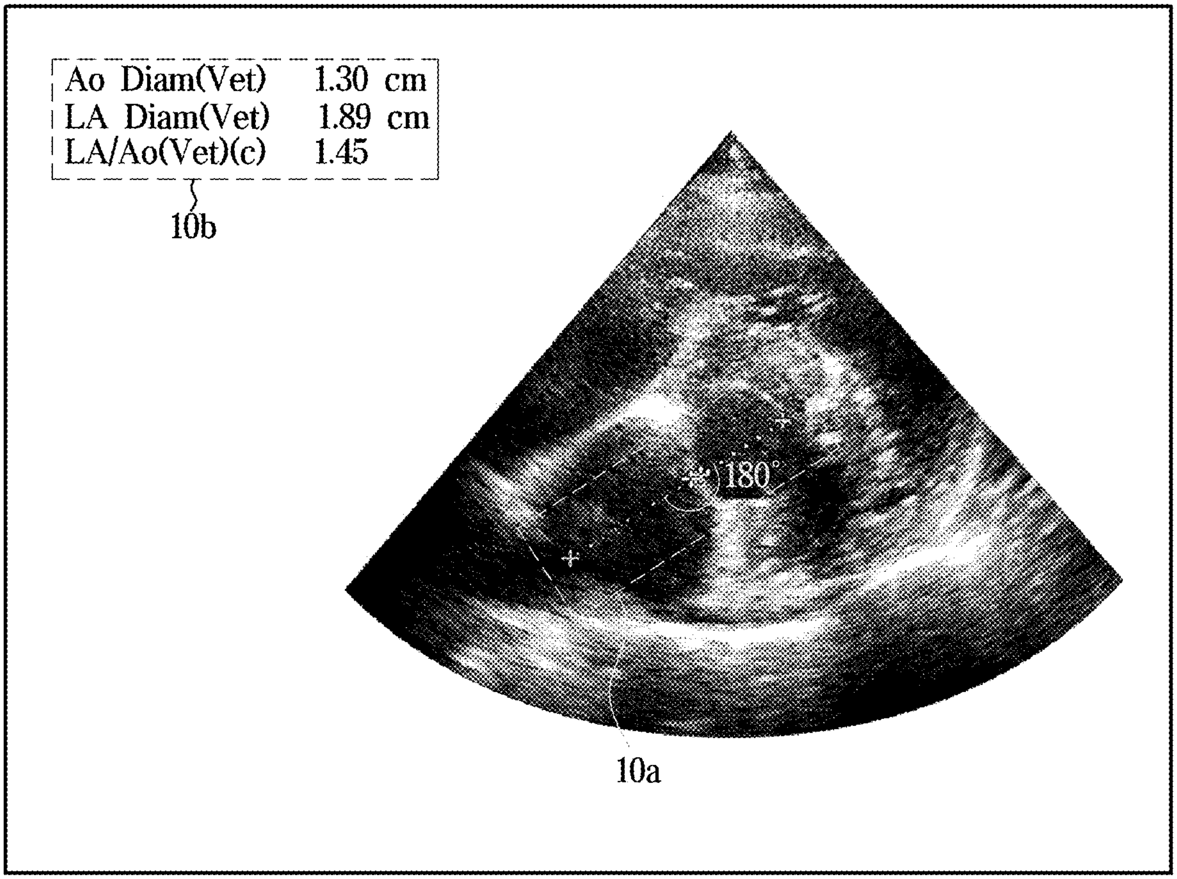
FIG. 16 is a diagram illustrating an image displayed on a display of an ultrasonic diagnostic apparatus according to an example of the standardized method of obtaining the length information of the plurality of target structures from the processed image.

FIG. 16 is a diagram illustrating an image displayed on a display of an ultrasonic diagnostic apparatus according to an example of the standardized method of obtaining the length information of the plurality of target structures from the processed image.

According to an embodiment, the processor 120 may display the obtained length information together with a cross-sectional image. In this case, the cross-sectional image may include a cross-sectional image obtained from an ultrasonic image and input as input data to the AI model.

Referring to FIG. 16, the processor 120 may control the display to display a diameter of the left atrium cross-section, the diameter of the aorta, or the diameter ratio of the left atrium and the aorta together with the cross-section image.

In this case, the processor 120 may display the diameter of the left atrium cross-section, the diameter of the aorta, or the diameter ratio of the left atrium and the aorta as an annotation 10*b* on one side of the cross-section image. In the present disclosure, the annotation regarding the diameter of the left atrium cross-section, the diameter of the aorta, or the diameter ratio of the left atrium and the aorta is displayed at an upper left corner of the screen of the display 140, but this is only an example and the location thereof may be changed as long as the cross-section image is not covered.

The processor 120 may also display the diameter of the left atrial cross-section, the diameter of the aorta, or the diameter ratio of the left atrial and the aorta, together with an iconographic indicator and a numerical value. For example, an iconographic indicator 10*a* displayed with a numerical value may include a first indicator indicating intersection points between one line passing through the centers of gravity of the respective contouring images of the left atrium and the aorta and the respective boundaries of the contouring images, and a second indicator indicating a connecting line connecting the intersection points in the respective contouring images.

Figure 17:
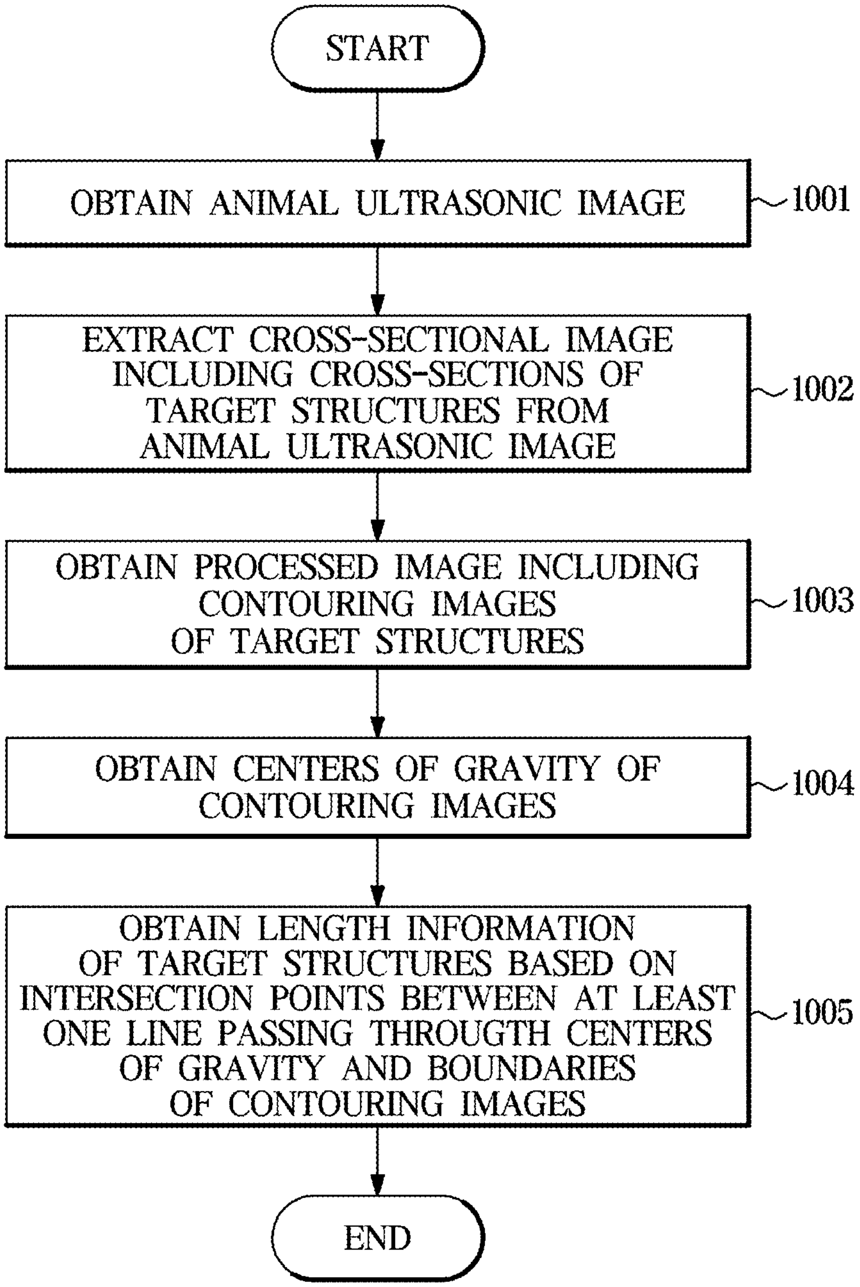
FIG. 17 is a control flowchart of the ultrasonic diagnostic apparatus according to an embodiment.

FIG. 17 is a control flowchart of the ultrasonic diagnostic apparatus according to an embodiment.

According to an embodiment, the processor 120 may obtain an animal ultrasonic image (1001). In this case, the animal ultrasonic image may include a real-time ultrasonic image obtained based on an echo signal returned by reflecting an ultrasonic signal emitted from the probe 20 to the object. The animal ultrasonic image may also be an ultrasonic image stored in the memory 150.

The processor 120 may extract a cross-sectional image including cross-sections of target structures from the animal ultrasonic image (1002). In this case, the target structure may include a structure that is the target of measurement to obtain length information. For example, in obtaining information on the diameter of the left atrium, the target structure may be a cross section of the left atrium. Also, in obtaining information on the diameter of the aorta, the target structure may be a cross section of the aorta. As another example, in obtaining information about the diameter ratio of the left atrium and the aorta, the target structure may be the cross section of the left atrium and the cross section of the aorta. The target structure may be determined based on the user input received from the input interface 170. For example, the user may directly set a target structure (e.g., an organ, lesion, tumor, etc.) through the input interface 170. The processor 120 may also determine a preset target structure as the target structure based on the mode or application selected by the user through the input interface 170.

The processor 120 may obtain a processed image including contouring images of target structures from the extracted cross-sectional image (1003). Specifically, the processor 120 may input the extracted cross-sectional image as input data to the AI model and obtain a processed image as output data. The AI model may be stored in the memory 150.

In this case, in training the AI model used to obtain the processed image, the machine learning model may be learned by using a cross-sectional image including cross-sections of a plurality of target structures as input data, and an image indicating the boundaries of the respective target structures capable of being checked in the cross-sectional image including the cross-sections of the plurality of target structures as training data.

In addition, the machine learning model may be learned by adding an image indicating the boundaries of the respective target structures, in which the characteristic factors of the target structures are reflected, as training data to the cross-sectional image including the cross-sections of the plurality of target structures. Accordingly, the AI model may be learned to obtain more generalized output data by using the correct answer data labeled with two criteria as correct answer data.

The processor 120 may obtain a center of gravity of each of the contouring images included in the obtained processed image (1004). In this case, a known image processing method may be used as a method in which the processor 120 calculates the center of gravity of each contouring image. As an example, the processor 120 may binarize contouring images and calculate the coordinate values of all pixels belonging to the binarized contouring images by a taking weighted average. That is, the processor 120 may calculate the center of gravity by adding up the product of coordinates of each pixel and a pixel value for each of x and y axes and dividing this by the total number of pixels of a structure.

Accordingly, the processor 120 may obtain length information of the target structures based on intersection points between at least one line passing through the centers of gravity of the contouring images and the boundaries of the contouring images (1005). In this case, the length information may include a length, diameter, width or diameter ratio. For example, the processor 120 may calculate the diameter of the left atrium, the diameter of the aorta, or the diameter ratio of the left atrium and the aorta based on the intersection points between one line passing through the centers of gravity of the respective contouring images of the left atrium and the aorta and the boundaries of the contouring images.

Specifically, the processor 120 may calculate the diameter of the left atrium using two intersection points between one line passing through all centers of gravity and the boundary of the left atrium contouring image as reference points. The processor 120 may also calculate the diameter of the aorta using two intersection points between one line passing through all centers of gravity and the boundary of the aortacontouring image as reference points. Thereafter, the processor 120 may calculate the diameter ratio of the left atrium and the aorta.

A control method of an ultrasonic diagnostic apparatus according to an embodiment may include obtaining an animal ultrasonic image, extracting a cross-sectional image including cross sections of a plurality of target structures from the animal ultrasonic image, obtaining a processed image including contouring images of the plurality of target structures from the cross-sectional image, obtaining a center of gravity of each of the contouring images, and obtaining length information of the target structures based on intersection points between at least one line passing through centers of gravity of the contouring images and boundaries of the contouring images.

The target structures may include a left atrium and an aorta.

The obtaining of the length information of the target structures may include obtaining a diameter of the left atrium, a diameter of the aorta, or a diameter ratio of the left atrium and the aorta.

The obtaining of the diameter of the left atrium, the diameter of the aorta, or the diameter ratio of the left atrium and the aorta may include calculating the diameter of the left atrium, the diameter of the aorta, or the diameter ratio of the left atrium and the aorta based on the intersection points between one line passing through all the centers of gravity of the respective contouring images of the left atrium and the aorta and the boundaries of the respective contouring images.

The control method of the ultrasonic diagnostic apparatus may further include displaying the diameter of the left atrium, the diameter of the aorta, or the diameter ratio of the left atrium and the aorta together with the cross-sectional image.

The displaying of the diameter of the left atrium, the diameter of the aorta, or the diameter ratio of the left atrium and the aorta together with the cross-sectional image may include displaying the diameter of the left atrium, the diameter of the aorta, or the diameter ratio of the left atrium and the aorta as an annotation on one side of the cross-sectional image.

The displaying of the diameter of the left atrium, the diameter of the aorta, or the diameter ratio of the left atrium and the aorta together with the cross-sectional image may include displaying an iconographic indicator and a numerical value of the diameter of the left atrium, the diameter of the aorta, or the diameter ratio of the left atrium and the aorta.

In this case, the iconographic indicator may include a first indicator indicating the intersection points between one line passing through all the centers of gravity of the respective contouring images of the left atrium and the aorta and the boundaries of the respective contouring images, and a second indicator indicating a connecting line connecting the intersection points in the respective contouring images.

The obtaining of the the processed image including contouring images of the plurality of target structures from the cross-sectional image may include inputting a cross-sectional image including cross sections of the plurality of target structures obtained from the animal ultrasonic image as input data to an AI model stored in memory and obtaining a processed image including the contouring images of the plurality of target structures as output data.

The control method of the ultrasonic diagnostic apparatus may further include training the AI model by using the cross-sectional image including the cross sections of the plurality of target structures as input data and an image indicating the boundaries of the respective target structures capable of being checked in the cross-sectional image including the cross sections of the plurality of target structures as training data.

The control method of the ultrasonic diagnostic apparatus may further include training the AI model by adding an image indicating the boundaries of the respective target structures, in which characteristic factors of the target structures are reflected, as training data to the cross-sectional image including the cross sections of the plurality of target structures.

An ultrasonic diagnostic apparatus according to an embodiment may include a probe configured to transmit an ultrasonic signal to an object and receive an echo signal reflected from the object, a display configured to display an ultrasonic image obtained based on echo information received by the probe, an input interface configured to receive user input, and a processor configured to control the probe to obtain an animal ultrasonic image, extract a cross-sectional image including cross sections of a plurality of target structures from the animal ultrasonic image, obtain a processed image including contouring images of the plurality of target structures from the cross-sectional image, obtain a center of gravity of each of the contouring images, and obtain length information of the target structures based on intersection points between at least one line passing through centers of gravity of the contouring images and boundaries of the contouring images.

The target structures may include a left atrium and an aorta.

The length information of the target structures may include a diameter of the left atrium, a diameter of the aorta, or a diameter ratio of the left atrium and the aorta.

The processor may be configured to calculate the diameter of the left atrium, the diameter of the aorta, or the diameter ratio of the left atrium and the aorta based on the intersection points between one line passing through all the centers of gravity of the respective contouring images of the left atrium and the aorta and the boundaries of the respective contouring images.

The processor may be configured to control the display to display the diameter of the left atrium, the diameter of the aorta, or the diameter ratio of the left atrium and the aorta together with the cross-sectional image.

The processor may be configured to control the display to display the diameter of the left atrium, the diameter of the aorta, or the diameter ratio of the left atrium and the aorta as an annotation on one side of the cross-sectional image.

The processor may be configured to control the display to display an iconographic indicator and a numerical value of the diameter of the left atrium, the diameter of the aorta, or the diameter ratio of the left atrium and the aorta.

In this case, the iconographic indicator may include a first indicator indicating the intersection points between one line passing through all the centers of gravity of the respective contouring images of the left atrium and the aorta and the boundaries of the respective contouring images, and a second indicator indicating a connecting line connecting the intersection points in the respective contouring images.

The ultrasonic diagnostic apparatus may include memory provided to store an AI model, wherein the processor may be configured to input a cross-sectional image including cross sections of the plurality of target structures obtained from the animal ultrasonic image as input data to the AI model stored in the memory and obtain a processed image including the contouring images of the plurality of target structures as output data.

The processor may be configured to learn the AI model by using the cross-sectional image including the cross sections of the plurality of target structures as input data and an image indicating the boundaries of the respective target structures capable of being checked in the cross-sectional image including the cross sections of the plurality of target structures as training data.

The processor may be configured to learn the AI model by adding an image indicating the boundaries of the respective target structures, in which characteristic factors of the target structures are reflected, as training data to the cross-sectional image including the cross sections of the plurality of target structures.

According to an aspect of the disclosure, factors causing inter-veterinarian and inter measurement-attempt errors can be eliminated by measuring a diameter ratio of a left atrium and an aorta with a standardized method.

According to an aspect of the disclosure, the accuracy of diagnosis can be improved.

However, effects that may be achieved by the ultrasonic diagnostic apparatus and the control method thereof of this disclosure are not limited to the effects mentioned above, and other effects not mentioned may be clearly understood by those skilled in the art to which the disclosure belongs from the above description. The disclosed embodiments may be implemented in the form of a recording medium storing instructions executable by a computer. The instructions may be stored in the form of program code, and when executed by a processor, a program module may be created to perform the operations of the disclosed embodiments. The recording medium may be implemented as a computer-readable recording medium.

A computer-readable recording medium includes any type of recording medium in which instructions readable by the computer are stored. For example, the recording medium may include a read only memory (ROM), a random access memory (RAM), a magnetic tape, a magnetic disk, a flash memory, an optical data storage device, and the like.

The computer-readable recording medium may be provided in the form of a non-transitory storage medium. Herein, the 'non-transitory storage medium' simply means that it is a tangible device and does not contain signals (e.g. electromagnetic waves), and this term does not distinguish between a case where data is semi-permanently stored in a storage medium and a case where data is stored temporarily. For example, the 'non-transitory storage medium' may include a buffer where data is temporarily stored.

According to an embodiment, the methods according to various embodiments disclosed in this document may be included and provided in a computer program product. The computer program product is a commodity and may be traded between sellers and buyers. The computer program product may be distributed in the form of a machine-readable recording medium (e.g., compact disc read only memory (CD-ROM)), or may be distributed (e.g., downloaded or uploaded) online, through an application store (e.g., Play Store™) or directly between two user devices (e.g., smartphones). In the case of online distribution, at least a portion of the computer program product (e.g., a downloadable app) may be at least temporarily stored or created temporarily in the machine-readable recording medium, such as the memory of a manufacturer server, an application store server, and a relay server.

The foregoing has illustrated and described the specific embodiments. However, it should be understood by those of skilled in the art that the disclosure is not limited to the above-described embodiments, and various changes and modifications may be made without departing from the technical idea of the disclosure described in the claims.

What is claimed is:

1. A control method of an ultrasonic diagnostic apparatus, the control method being performed by a processor and comprising:

controlling a probe to transmit an ultrasonic signal to an object and to receive an echo signal reflected from the object;

obtaining an animal ultrasonic image based on the received echo signal;

extracting, from the animal ultrasonic image, a cross-sectional image comprising cross sections of a left atrium and an aorta;

inputting the cross-sectional image as input data to an artificial intelligence model, and obtaining, as output data of the artificial intelligence model, a contouring image of the left atrium and a contouring image of the aorta;

obtaining a center of gravity of each of the contouring image of the left atrium and the contouring image of the aorta;

determining one line passing through both the center of gravity of the contouring image of the left atrium and the center of gravity of the contouring image of the aorta;

obtaining intersection points between the one line and a boundary of the contouring image of the left atrium and a boundary of the contouring image of the aorta;

calculating a diameter of the left atrium based on a distance between the intersection points on the boundary of the contouring image of the left atrium, a diameter of the aorta based on a distance between the intersection points on the boundary of the contouring image of the aorta, and a diameter ratio of the left atrium and the aorta; and controlling a display to display the calculated diameter ratio together with the cross-sectional image.

2. The control method according to claim 1, wherein the controlling the display comprises:

displaying the diameter of the left atrium, the diameter of the aorta, er and the diameter ratio of the left atrium and the aorta as an annotation on one side of the cross-sectional image.

3. The control method according to claim 1, wherein the controlling the display comprises:

displaying an iconographic indicator and a numerical value of the diameter of the left atrium, the diameter of the aorta, and the diameter ratio of the left atrium and the aorta, and wherein the iconographic indicator comprises a first indicator indicating the intersection points between the one line and each of the boundary of the contouring image of the left atrium and the boundary of the contouring image of the aorta, and a second indicator indicating a connecting line connecting the intersection points in the contouring image of the left atrium and the contouring image of the aorta, respectively.

4. The control method according to claim 1, further comprising training the artificial intelligence model by using the cross-sectional image comprising the cross sections of the plurality of target structures including the left atrium and the aorta as input data and an image indicating the boundaries of the respective target structures capable of being checked in the cross-sectional image as training data.

5. The control method according to claim 4, further comprising training the artificial intelligence model by adding an image indicating the boundaries of the respective target structures, in which characteristic factors of the target structures are reflected, as training data to the cross-sectional image comprising the cross sections of the plurality of target structures.

6. An ultrasonic diagnostic apparatus comprising:

a probe configured to transmit an ultrasonic signal to an object and receive an echo signal reflected from the object;

a display;

an input interface configured to receive user input; and a processor configured to:

obtain an animal ultrasonic image based on the received echo signal, extract from the animal ultrasonic image, a cross-sectional image comprising cross sections of a left atrium and an aorta, input the cross-sectional image as input data to an artificial intelligence model, and obtain, as output data of the artificial intelligence model, a contouring image of the left atrium and a contouring image of the aorta, obtain a center of gravity of each of the contouring image of the left atrium and the contouring image of the aorta, determine one line passing through both the center of gravity of the contouring image of the left atrium and the center of gravity of the contouring image of the aorta, obtain intersection points between the one line and a boundary of the contouring image of the left atrium and a boundary of the contouring image of the aorta, calculate a diameter of the left atrium based on a distance between the intersection points on the boundary of the contouring image of the left atrium, a diameter of the aorta based on a distance between the intersection points on the boundary of the contouring image of the aorta, and a diameter ratio of the left atrium and the aorta, and control the display to display the calculated diameter ratio together with the cross-sectional image.

7. The ultrasonic diagnostic apparatus according to claim 6, wherein the processor is configured to control the display to display the diameter of the left atrium, the diameter of the aorta, and the diameter ratio of the left atrium and the aorta as an annotation on one side of the cross-sectional image.

8. The ultrasonic diagnostic apparatus according to claim 6, wherein the processor is configured to control the display to display an iconographic indicator and a numerical value of the diameter of the left atrium, the diameter of the aorta, and the diameter ratio of the left atrium and the aorta, and the iconographic indicator comprises a first indicator indicating the intersection points between the one line and each of the boundary of the contouring image of the left atrium and the boundary of the contouring image of the aorta, and a second indicator indicating a connecting line connecting the intersection points in the contouring image of the left atrium and the contouring image of the aorta, respectively.

9. The ultrasonic diagnostic apparatus according to claim 6, wherein the processor is configured to train the artificial intelligence model by using the cross-sectional image comprising the cross sections of the plurality of target structures including the left atrium and the aorta as input data and an image indicating the boundaries of the respective target structures capable of being checked in the cross-sectional image as training data.

10. The ultrasonic diagnostic apparatus according to claim 9, wherein the processor is configured to train the artificial intelligence model by adding an image indicating the boundaries of the respective target structures, in which characteristic factors of the target structures are reflected, as training data to the cross-sectional image comprising the cross sections of the plurality of target structures.

* * * * *